(12) United States Patent
Shelton, IV et al.

(10) Patent No.: US 11,744,587 B2
(45) Date of Patent: Sep. 5, 2023

(54) POWERED SURGICAL INSTRUMENT WITH INDEPENDENT SELECTIVELY APPLIED ROTARY AND LINEAR DRIVETRAINS

(71) Applicant: Cilag GmbH International, Zug (CH)

(72) Inventors: Frederick E. Shelton, IV, Hillsboro, OH (US); Jason L. Harris, Lebanon, OH (US); Michael J. Vendely, Lebanon, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 17/090,402

(22) Filed: Nov. 5, 2020

(65) Prior Publication Data

US 2021/0169477 A1 Jun. 10, 2021

Related U.S. Application Data

(63) Continuation of application No. 15/634,524, filed on Jun. 27, 2017, now Pat. No. 10,888,324.

(51) Int. Cl.
*A61B 17/072* (2006.01)
*A61B 17/115* (2006.01)
(Continued)

(52) U.S. Cl.
CPC .. *A61B 17/07207* (2013.01); *A61B 17/00234* (2013.01); *A61B 17/072* (2013.01);
(Continued)

(58) Field of Classification Search
CPC .......................... A61B 17/072; A61B 17/1155
See application file for complete search history.

(56) References Cited

U.S. PATENT DOCUMENTS 5,467,911 A 11/1995 Tsuruta et al.
6,783,524 B2 8/2004 Anderson et al.
(Continued)

FOREIGN PATENT DOCUMENTS

CA 2890787 A1 12/2006
EP 2377471 A1 10/2011
(Continued)

OTHER PUBLICATIONS

Extended European Search Report dated Aug. 23, 2018, for Application No. 18180214.1, 13 pages.
(Continued)

*Primary Examiner* — Nathaniel C Chukwurah
(74) *Attorney, Agent, or Firm* — Frost Brown Todd LLP

(57) ABSTRACT

An apparatus includes a body and a shaft assembly. The body includes a rotary drive output, a linear drive output, and a control module. The shaft assembly includes a distal end and a proximal end. The distal end includes a type of end effector configured to operate on tissue. The proximal end is configured to removably couple with the body assembly. The proximal end includes one or both of a rotary drive input configured to couple with the rotary drive output or a linear drive input configured to couple with the linear drive input. The shaft assembly is configured to actuate the end effector in response to movement of one or both of the rotary drive input or the linear drive input. The control module is configured to selectively actuate the rotary drive output or the linear drive output based on the type of end effector of the shaft assembly.

20 Claims, 16 Drawing Sheets

(51) Int. Cl.
    *A61B 17/00* (2006.01)
    *A61B 90/00* (2016.01)
    *A61B 17/29* (2006.01)
    *A61B 90/98* (2016.01)

(52) U.S. Cl.
    CPC ........... *A61B 17/1155* (2013.01); *A61B 90/98* (2016.02); *A61B 2017/00017* (2013.01); *A61B 2017/0046* (2013.01); *A61B 2017/00199* (2013.01); *A61B 2017/00367* (2013.01); *A61B 2017/00389* (2013.01); *A61B 2017/00398* (2013.01); *A61B 2017/00464* (2013.01); *A61B 2017/00734* (2013.01); *A61B 2017/07221* (2013.01); *A61B 2017/07285* (2013.01); *A61B 2017/2903* (2013.01); *A61B 2090/0811* (2016.02)

(56) References Cited

U.S. PATENT DOCUMENTS

| | | |
|---|---|---|
| 7,000,818 B2 | 2/2006 | Shelton, IV et al. |
| 7,380,696 B2 | 6/2008 | Shelton, IV et al. |
| 7,404,508 B2 | 7/2008 | Smith et al. |
| 7,434,715 B2 | 10/2008 | Shelton, IV et al. |
| 7,721,930 B2 | 5/2010 | McKenna et al. |
| 8,408,439 B2 | 4/2013 | Huang et al. |
| 8,453,914 B2 | 6/2013 | Laurent et al. |
| 9,072,535 B2 | 7/2015 | Shelton, IV et al. |
| 9,186,142 B2 | 11/2015 | Fanelli et al. |
| 9,717,497 B2 | 8/2017 | Zerkle et al. |
| 9,795,379 B2 | 10/2017 | Leimbach et al. |
| 9,808,248 B2 | 11/2017 | Hoffman |
| 10,090,616 B1 | 10/2018 | Leimbach et al. |
| 10,163,309 B1 | 12/2018 | Shelton, IV et al. |
| 10,511,065 B2 | 12/2019 | Shelton, IV et al. |
| 10,639,018 B2 | 5/2020 | Shelton, IV et al. |
| 10,667,812 B2 | 6/2020 | Swensgard et al. |
| 10,828,029 B2 | 11/2020 | Auld et al. |
| 10,835,218 B2 | 11/2020 | Shelton, IV et al. |
| 10,888,324 B2 * | 1/2021 | Shelton, IV ......... A61B 17/072 |
| 10,987,103 B2 | 4/2021 | Shelton, IV et al. |
| 11,071,548 B2 | 7/2021 | Auld et al. |
| 2008/0255413 A1 | 10/2008 | Zemlok et al. |
| 2014/0110456 A1 | 4/2014 | Taylor |
| 2014/0246471 A1 | 9/2014 | Jaworek et al. |
| 2014/0263541 A1 | 9/2014 | Leimbach et al. |
| 2014/0309666 A1* | 10/2014 | Shelton, IV ......... A61B 17/072 606/139 |
| 2015/0083773 A1 | 3/2015 | Measamer et al. |
| 2015/0272575 A1 | 10/2015 | Leimbach et al. |
| 2015/0280384 A1 | 10/2015 | Leimbach et al. |
| 2016/0249917 A1 | 9/2016 | Beckman et al. |
| 2016/0249945 A1 | 9/2016 | Shelton, IV et al. |
| 2016/0345966 A1 | 12/2016 | Zemlok et al. |
| 2017/0079647 A1 | 3/2017 | Yates et al. |
| 2017/0086823 A1 | 3/2017 | Leimbach et al. |
| 2018/0168681 A1 | 6/2018 | Kirk et al. |
| 2018/0168745 A1 | 6/2018 | Overmyer et al. |

FOREIGN PATENT DOCUMENTS

| | | |
|---|---|---|
| EP | 2792313 A2 | 10/2014 |
| EP | 3225176 A1 | 10/2017 |
| JP | 2009-045452 A | 3/2009 |
| JP | 2016-509524 A | 3/2016 |
| JP | 2016-518920 A | 6/2016 |

OTHER PUBLICATIONS

International Search Report and Written Opinion dated Aug. 23, 2018, for International Application No. PCT/IB2018/053585, 22 pages.
Japanese Notification of Reasons for Refusal dated Apr. 28, 2022, for Application No. 2019-571457, 6 pages.
Chinese Office Action, The First Office Action, and Search Report dated Aug. 3, 2022 for Application No. CN 201880043329.2, 12 pgs.

* cited by examiner

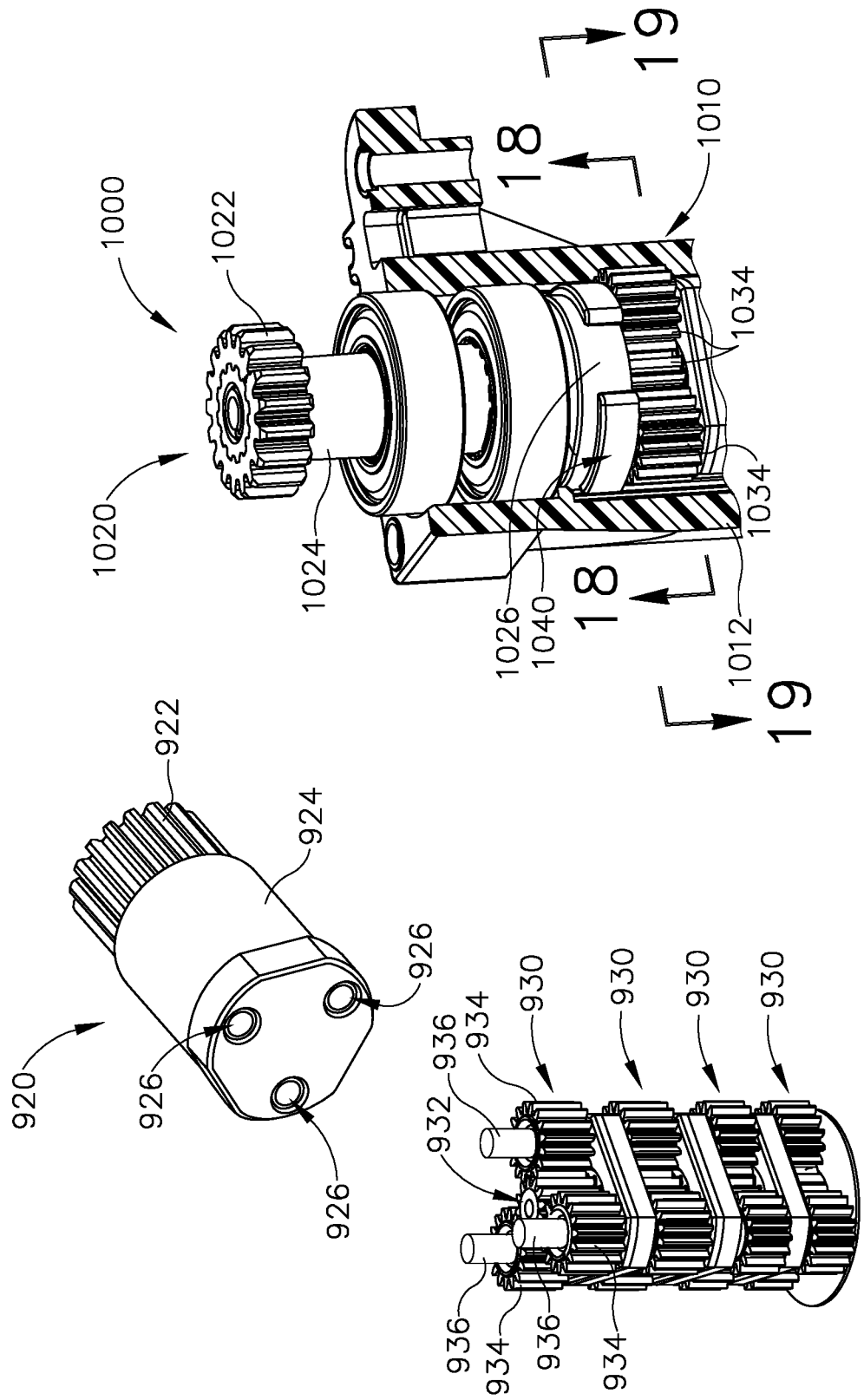

POWERED SURGICAL INSTRUMENT WITH INDEPENDENT SELECTIVELY APPLIED ROTARY AND LINEAR DRIVETRAINS

This application is a continuation of U.S. patent application Ser. No. 15/634,524, filed Jun. 27, 2017 and issued as U.S. Pat. No. 10,888,324 on Jan. 12, 2021.

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in various ways to achieve a diagnostic or therapeutic effect (e.g., endocutter, grasper, cutter, stapler, clip applier, access device, drug/gene therapy delivery device, and energy delivery device using ultrasonic vibration, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 7,000,818, entitled "Surgical Stapling Instrument Having Separate Distinct Closing and Firing Systems," issued Feb. 21, 2006; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. patents is incorporated by reference herein.

While the surgical staplers referred to above are described as being used in endoscopic procedures, such surgical staplers may also be used in open procedures and/or other non-endoscopic procedures. By way of example only, a surgical stapler may be inserted through a thoracotomy, and thereby between a patient's ribs, to reach one or more organs in a thoracic surgical procedure that does not use a trocar as a conduit for the stapler. Such procedures may include the use of the stapler to sever and close a vessel leading to a lung. For instance, the vessels leading to an organ may be severed and closed by a stapler before removal of the organ from the thoracic cavity. Of course, surgical staplers may be used in various other settings and procedures.

Examples of surgical staplers that may be particularly suited or use through a thoracotomy are disclosed in U.S. Patent Application Publication No. 2014/0243801, entitled "Surgical Instrument End Effector Articulation Drive with Pinion and Opposing Racks," published on Aug. 28, 2014, issued as U.S. Pat. No. 9,186,142 on Nov. 17, 2015; U.S. Patent Application Publication No. 2014/0239041, entitled "Lockout Feature for Movable Cutting Member of Surgical Instrument," Published Aug. 28, 2014, issued as U.S. Pat. No. 9,717,497 on Aug. 1, 2017; U.S. Patent Application Publication No. 2014/0239038, entitled "Surgical Instrument with Multi-Diameter Shaft," published Aug. 28, 2014, issued as U.S. Pat. No. 9,795,379 on Oct. 24, 2017; and U.S. Patent Application Publication No. 2014/0239044, entitled "Installation Features for Surgical Instrument End Effector Cartridge," published Aug. 28, 2014, issued as U.S. Pat. No. 9,808,248 on Nov. 7, 2017. The disclosure of each of the above-cited U.S. Patent Applications is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 16 depicts a partially exploded perspective view of planetary gears and a drive shaft of the rotary drive assembly of FIG. 14;

FIG. 17 depicts a partial perspective view of another exemplary rotary drive assembly that may be incorporated into a surgical instrument;

Figure 1:
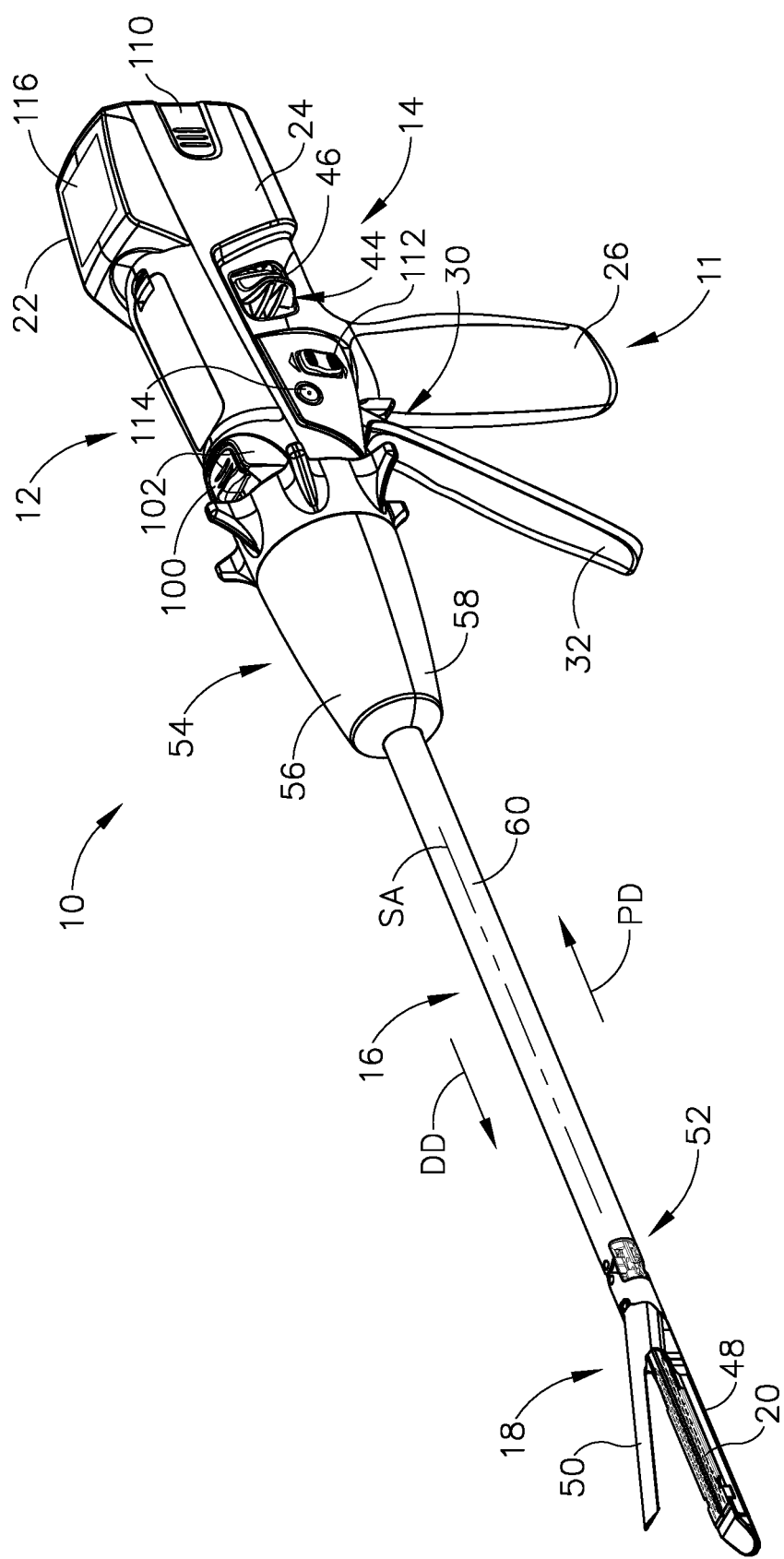
FIG. 1 depicts a perspective view of an exemplary surgical instrument including an interchangeable shaft assembly and a handle assembly.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to an operator or other operator grasping a surgical instrument having a distal surgical end effector. The term "proximal" refers the position of an element closer to the operator or other operator and the term "distal" refers to the position of an element closer to the surgical end effector of the surgical instrument and further away from the operator or other operator. Although the surgical instruments described herein comprise motorized implements for cutting and stapling, it will be appreciated that the configurations described herein may be used with any suitable type of electrical surgical instrument such as cutters, claspers, staplers, RF cutter/coagulators, ultrasonic cutter/coagulators, and laser cutter/coagulators, for example.

I. EXEMPLARY SURGICAL INSTRUMENT WITH LINEAR DRIVE ASSEMBLY

FIG. 1 depicts a motor-driven surgical cutting and fastening instrument (10) that includes a handle assembly (11) and a removable shaft assembly (16). In some versions, handle assembly (11) and shaft assembly (16) are each provided a single-use, disposable components. In some other versions, handle assembly (11) and shaft assembly (16) are each provided as reusable components. As another merely illustrative example, shaft assembly (16) may be provided as a single-use, disposable component while handle assembly is provided as a reusable component. Various suitable ways in which reusable versions of handle assembly (11) and shaft assembly (16) may be suitable reprocessed for reuse will be apparent to those of ordinary skill in the art in view of the teachings herein.

Handle assembly (11) of the present example includes a housing (12), a closure trigger (32), and a firing trigger (33). At least a portion of housing (12) forms a handle (14) that is configured to be grasped, manipulated and actuated by the clinician. Housing (12) is configured for operative attachment to shaft assembly (16), which has a surgical end effector (18) operatively coupled thereto. As described below, end effector (18) is configured to perform one or more surgical tasks or procedures. In particular, end effector (18) of the example shown in FIG. 1 is operable to perform a surgical cutting and stapling procedure, in a manner like an end effector of a conventional endocutter, though this is just one merely illustrative example.

Figure 2:
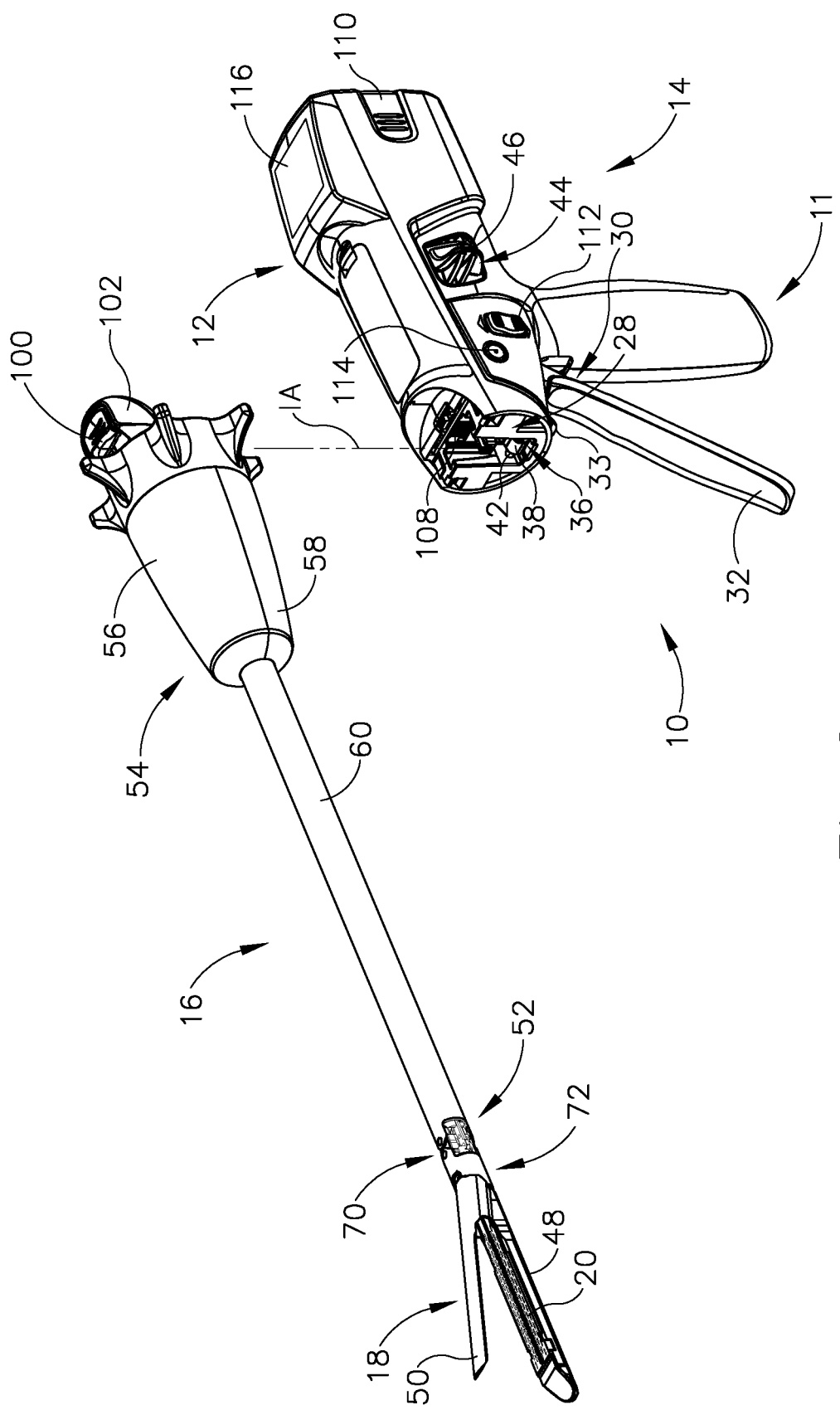
FIG. 2 depicts a perspective view of the instrument of FIG. 1, showing the shaft assembly disassembled from the handle assembly of the instrument.
Figure 3:
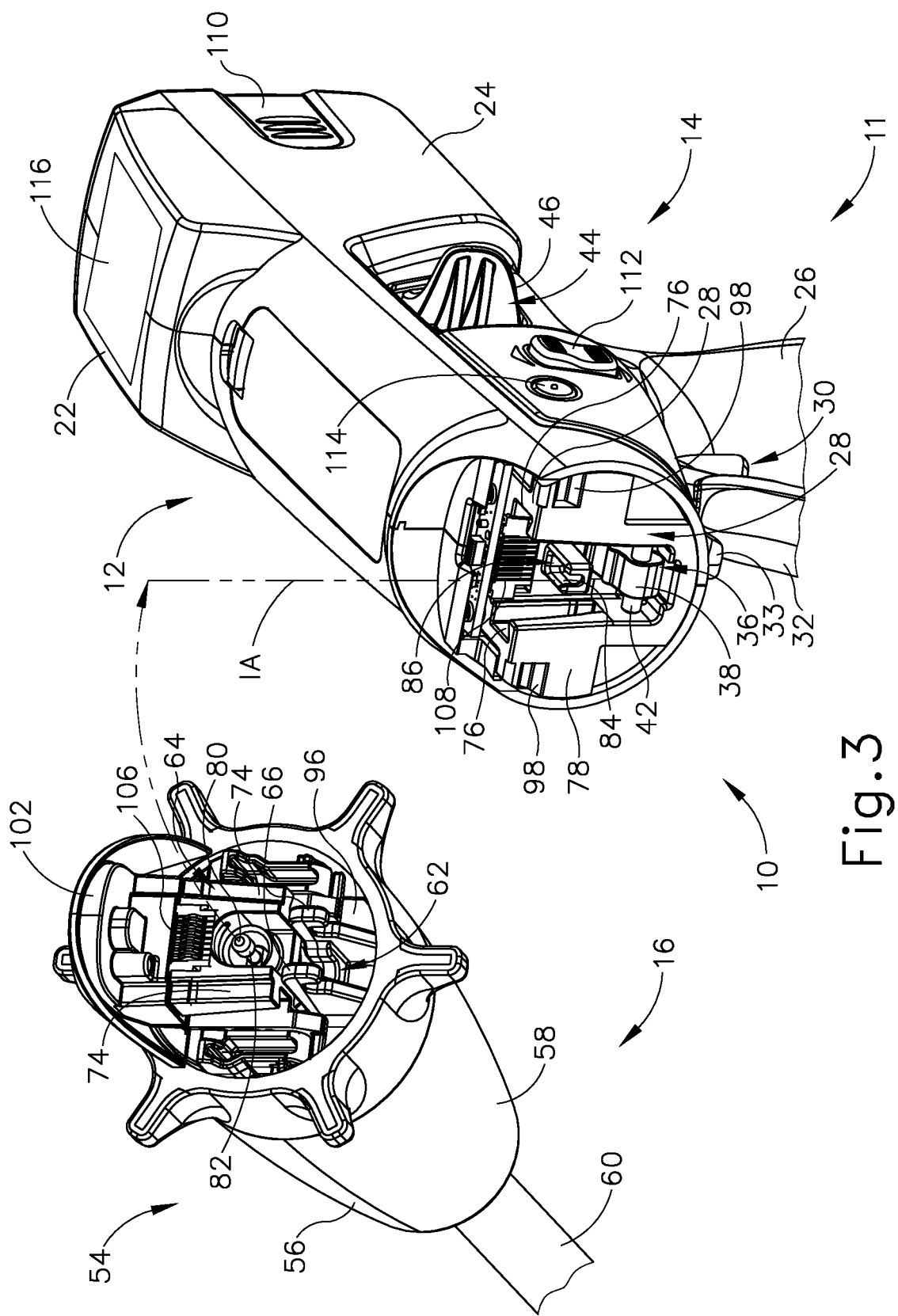
FIG. 3 depicts a partial perspective view of the instrument of FIG. 1, showing the shaft assembly disassembled from the handle assembly of the instrument.

FIG. 1 illustrates surgical instrument (10) with interchangeable shaft assembly (16) operatively coupled to handle assembly (11). FIGS. 2-3 illustrate attachment of interchangeable shaft assembly (16) to housing (12) of handle (14). Handle (14) includes a pair of interconnectable handle housing segments (22, 24) that may be interconnected by screws, snap features, adhesive, etc. In the illustrated arrangement, handle housing segments (22, 24) cooperate to form a pistol grip portion (26) that can be grasped and manipulated by the clinician. As will be discussed in further detail below, handle (14) operatively supports a plurality of drive systems therein that are configured to generate and apply various control motions to corresponding portions of interchangeable shaft assembly (16) that is operatively attached thereto. As will also be discussed in further detail below, triggers (32, 33) are pivotable toward pistol grip portion (26) to activate at least some of the drive systems in handle (14).

Figure 5:
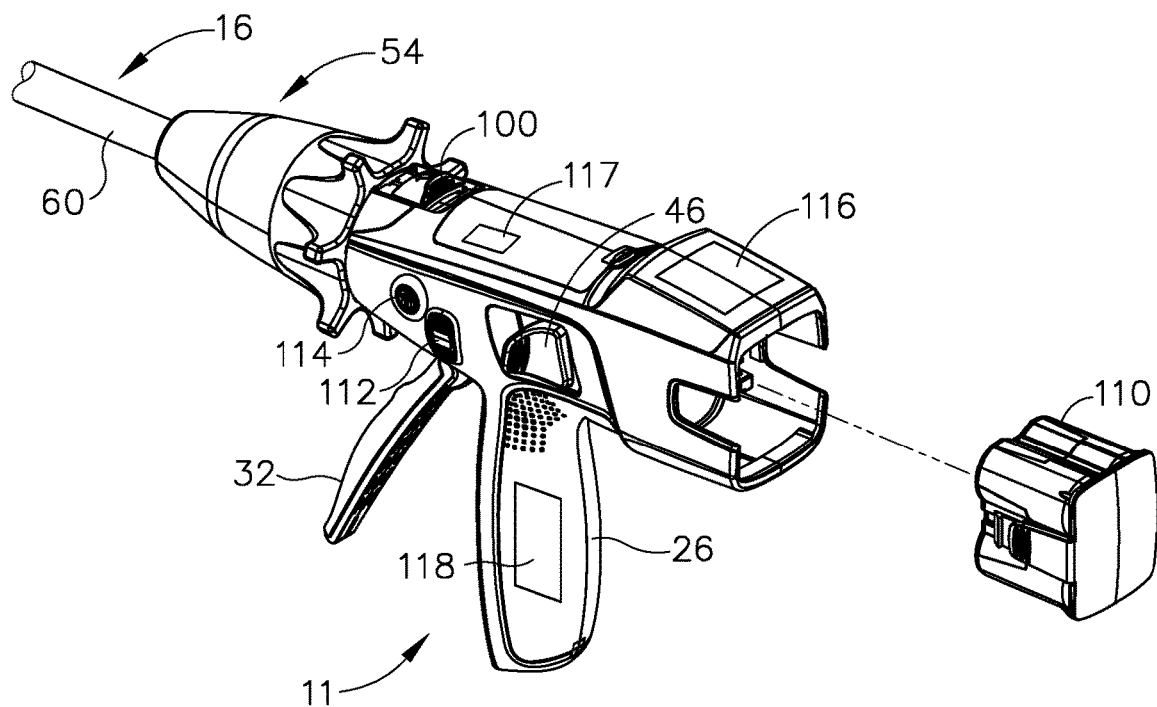
FIG. 5 depicts a perspective view of a proximal portion of the instrument of FIG. 1, with a battery removed from the handle assembly.

At least some of the drive systems in handle assembly (11) are ultimately driven by a motor (118), which is shown schematically in FIG. 5. In the present example, motor (118) is in pistol grip portion (26), though motor (118) may instead be located at any other suitable position. Motor (118) receives power from a battery pack (110), which is secured to handle (14). In the present example, and as shown in FIG. 5, battery pack (110) is removable from handle (14). In some other versions, battery pack (110) is not removable from handle (14). In some such versions, battery pack (110) (or a variation thereof) is fully contained within handle housing segments (22, 24). Various suitable forms that motor (118) and battery pack (110) may take will be apparent to those of ordinary skill in the art in view of the teachings herein.

As also shown schematically in FIG. 5, a control circuit (117) is contained within handle (14). By way of example only, control circuit (117) may comprise a microcontroller and/or various other components as will be apparent to those of ordinary skill in the art in view of the teachings herein. Control circuit (117) is configured to store and execute control algorithms to drive motor (118). Control circuit (117) is also configured to drive a graphical user interface (116), which is located at the proximal end of handle assembly (11). In some versions, control circuit (117) is configured to receive and process one or more signals from shaft assembly (16). By way of example only, control circuit (117) may be configured and operable in accordance with at least some of the teachings of U.S. Pub. No. 2015/0272575, entitled "Surgical Instrument Comprising a Sensor System," published Oct. 1, 2015, issued as U.S. Pat. No. 9,913,642 on Mar. 13, 2018, the disclosure of which is incorporated by reference herein. Other suitable ways in which control circuit (117) may be configured and operable will be apparent to those of ordinary skill in the art in view of the teachings herein.

As best seen in FIG. 3, a frame (28) of handle (14) operatively supports a plurality of drive systems. In this example, frame (28) operatively supports a "first" or closure drive system, generally designated as (30), which may be employed to apply closing and opening motions to interchangeable shaft assembly (16) that is operatively attached or coupled thereto. Also in this example, closure drive system (30) includes an actuator in the form of a closure trigger (32) that is pivotally supported by frame (28). More specifically, closure trigger (32) is pivotally coupled to housing (14) by a pin (not shown). Such arrangement enables closure trigger (32) to be manipulated by a clinician such that when the clinician grasps pistol grip portion (26) of handle (14), closure trigger (32) may be easily pivoted from a starting or "unactuated" position (FIG. 4A) toward pistol grip portion (26) to an "actuated" position; and more particularly to a fully compressed or fully actuated position (FIG. 4B). Closure trigger (32) may be biased into the unactuated position by spring or other biasing arrangement (not shown).

In the present example, closure drive system (30) further includes a closure linkage assembly (36) pivotally coupled to closure trigger (32). A portion of closure linkage assembly (36) is shown in FIG. 3. Closure linkage assembly (36) may include a first closure link (not shown) and a second closure link (38) that are pivotally coupled to closure trigger (32) by a pin (not shown). Second closure link (38) may also be referred to herein as an "attachment member" and includes a transverse attachment pin (42). As shown in FIG. 3, attachment pin (42) is exposed when shaft assembly (16) is detached from handle assembly (11). Attachment pin (42) may thus couple with a complementary feature of a shaft assembly (16) when shaft assembly (16) is coupled with handle assembly (11), as described in greater detail below.

Still referring to FIGS. 1-3, first closure link (not shown) is configured to cooperate with a closure release assembly (44) that is pivotally coupled to frame (28). In at least one example, closure release assembly (44) has a release button assembly (46) with a distally protruding locking pawl (not shown) formed thereon. Release button assembly (46) may be pivoted in a counterclockwise direction by a release spring (not shown). As the clinician depresses closure trigger (32) from its unactuated position toward pistol grip portion (26) of handle (14), first closure link (not shown) pivots upwardly to a point where a locking pawl (not shown) drops into retaining engagement with first closure link (not shown), thereby preventing closure trigger (32) from returning to the unactuated position. Thus, closure release assembly (44) serves to lock closure trigger (32) in the fully actuated position.

When the clinician desires to unlock closure trigger (32) from the actuated position to return to the unactuated position, the clinician simply pivots closure release button assembly (46) by urging release button assembly (46) distally, such that locking pawl (not shown) is moved out of engagement with the first closure link (not shown). When the locking pawl (not shown) has been moved out of engagement with first closure link (not shown), closure trigger (32) may return to the unactuated position in response to a resilient bias urging closure trigger (32) back to the unactuated position. Other closure trigger locking and release arrangements may also be employed.

Interchangeable shaft assembly (16) further includes an articulation joint (52) and an articulation lock (not shown) that can be configured to releasably hold end effector (18) in a desired position relative to a longitudinal axis of shaft assembly (16). In the present example, articulation joint (52) is configured to allow end effector (18) to be laterally deflected away from the longitudinal axis of shaft assembly (16), as is known in the art. By way of example only, end effector (18), articulation joint (52), and the articulation lock (not shown) may be configured and operable in accordance with at least some of the teachings of U.S. Pub. No. 2014/0263541, entitled "Articulatable Surgical Instrument Comprising an Articulation Lock," published Sep. 18, 2014 now abandoned.

In the present example, articulation at articulation joint (52) is motorized via motor (118), based on control input from the operator via an articulation control rocker (112) on handle assembly (11). By way of example only, when the operator presses on the upper portion of articulation control rocker (112), end effector (18) may laterally pivot to the right (viewing instrument (10) from above) at articulation joint (52); and when the operator presses on the lower portion of articulation control rocker (112), end effector (18) may laterally pivot to the left (viewing instrument (10) from above) at articulation joint (52). In some versions, the other side of handle assembly (11) includes another articulation control rocker (112). In such versions, the articulation control rocker (112) on the other side of handle assembly (11)

may be configured to provide pivoting of end effector (18) in directions opposite to those listed above in response to upper actuation of articulation control rocker (112) and lower actuation of articulation control rocker (112). By way of example only, articulation control rocker (112) and the rest of the features that provide motorized articulation of end effector (18) at articulation joint (52) may be configured and operable in accordance with at least some of the teachings of U.S. Pub. No. 2015/0280384, entitled "Surgical Instrument Comprising a Rotatable Shaft," published Oct. 1, 2015, issued as U.S. Pat. No. 10,201,364 on Feb. 12, 2019 the disclosure of which is incorporated by reference herein. Other suitable ways in which articulation control rocker (112) and the rest of the features that provide motorized articulation of end effector (18) at articulation joint (52) may be configured and operable will be apparent to those of ordinary skill in the art in view of the teachings herein.

End effector (18) of the present example comprises a lower jaw in the form of an elongated channel (48) that is configured to operatively a support staple cartridge (20) therein. End effector (18) of the present example further includes an upper jaw in the form of an anvil (50) that is pivotally supported relative to elongated channel (48). Interchangeable shaft assembly (16) further includes a proximal housing or nozzle (54) comprised of nozzle portions (56, 58); and a closure tube (60) that can be utilized to close and/or open anvil (50) of end effector (18). Shaft assembly (16) also includes a closure shuttle (62) that is slidably supported within a chassis (64) of shaft assembly (16) such that closure shuttle (62) may be axially moved relative to chassis (64). Closure shuttle (62) includes a pair of proximally-protruding hooks (66) that are configured for attachment to attachment pin (42) that is attached to second closure link (38). A proximal end (not shown) of closure tube (60) is coupled to closure shuttle (62) for relative rotation thereto, though the coupling of closure tube (60) with closure shuttle (62) provides that closure tube (60) and closure shuttle (62) will translate longitudinally with each other. A closure spring (not shown) is journaled on closure tube (60) and serves to bias closure tube (60) in the proximal direction (PD), which can serve to pivot closure trigger (32) into the unactuated position when shaft assembly (16) is operatively coupled to handle (14).

In the present example, articulation joint (52) includes a double pivot closure sleeve assembly (70). Double pivot closure sleeve assembly (70) includes an end effector closure sleeve assembly (72) for engaging an opening tab on anvil (50) in the various manners described in U.S. Pub. No. 2014/0263541, now abandoned, the disclosure of which is incorporated by reference herein. Double pivot closure sleeve assembly (70) is coupled with closure tube (60) such that double pivot closure sleeve assembly (70) translates with closure tube (60) in response to pivotal movement of closure trigger (32), even when articulation joint (52) is in an articulated state (i.e., when end effector (18) is pivotally deflected laterally away from the longitudinal axis of shaft assembly (16) at articulation joint (52)). Moreover, the engagement of end effector closure sleeve assembly (72) with anvil (50) provides pivotal movement of anvil (50) toward staple cartridge (20) in response to distal translation of double pivot closure sleeve assembly (70) and closure tube (60); and pivotal movement of anvil (50) away from staple cartridge (20) in response to proximal translation of double pivot closure sleeve assembly (70) and closure tube (60). While shaft assembly (16) of the present example includes articulation joint (52), other interchangeable shaft assemblies may lack articulation capabilities.

As shown in FIG. 3, chassis (64) includes a pair of tapered attachment portions (74) formed thereon that are adapted to be received within corresponding dovetail slots (76) formed within a distal attachment flange portion (78) of frame (28). Each dovetail slot (76) may be tapered or generally V-shaped to seatingly receive attachment portions (74) therein. A shaft attachment lug (80) is formed on the proximal end of an intermediate firing shaft (82). Thus, when interchangeable shaft assembly (16) is coupled to handle (14), shaft attachment lug (80) is received in a firing shaft attachment cradle (84) formed in a distal end of a longitudinal drive member (86). When shaft attachment lug (80) is received in firing shaft attachment cradle (84), intermediate firing shaft (82) will translate longitudinally with longitudinal drive member (86). When intermediate firing shaft (82) translates distally, intermediate firing shaft (82) actuates end effector (18) to drive staples into tissue and cut the tissue, as is known in the art. By way of example only, this actuation of end effector (18) may be carried out in accordance with at least some of the teachings of U.S. Pub. No. 2015/0280384, issued as U.S. Pat. No. 10,201,364, the disclosure of which is incorporated by reference herein; and/or in accordance with the teachings of various other references cited herein.

Figure 4A:
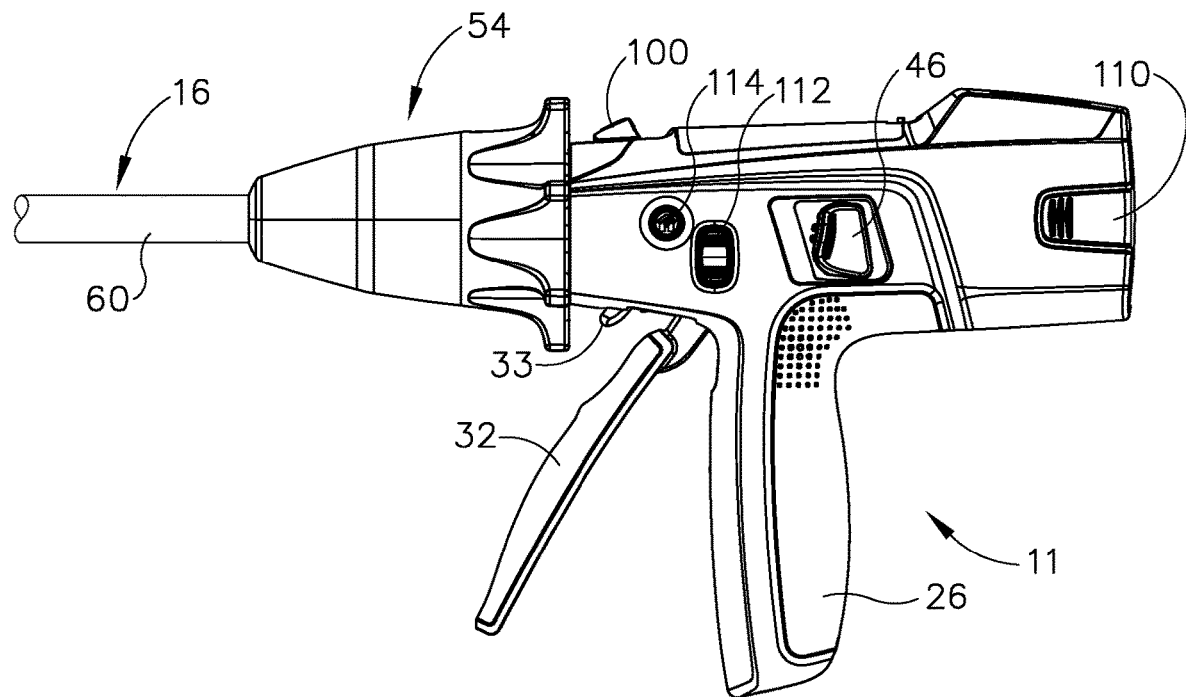
FIG. 4A depicts a side elevational view of a proximal portion of the instrument of FIG. 1, with a closure trigger in a first pivotal position and a firing trigger in a first pivotal position.
Figure 4B:
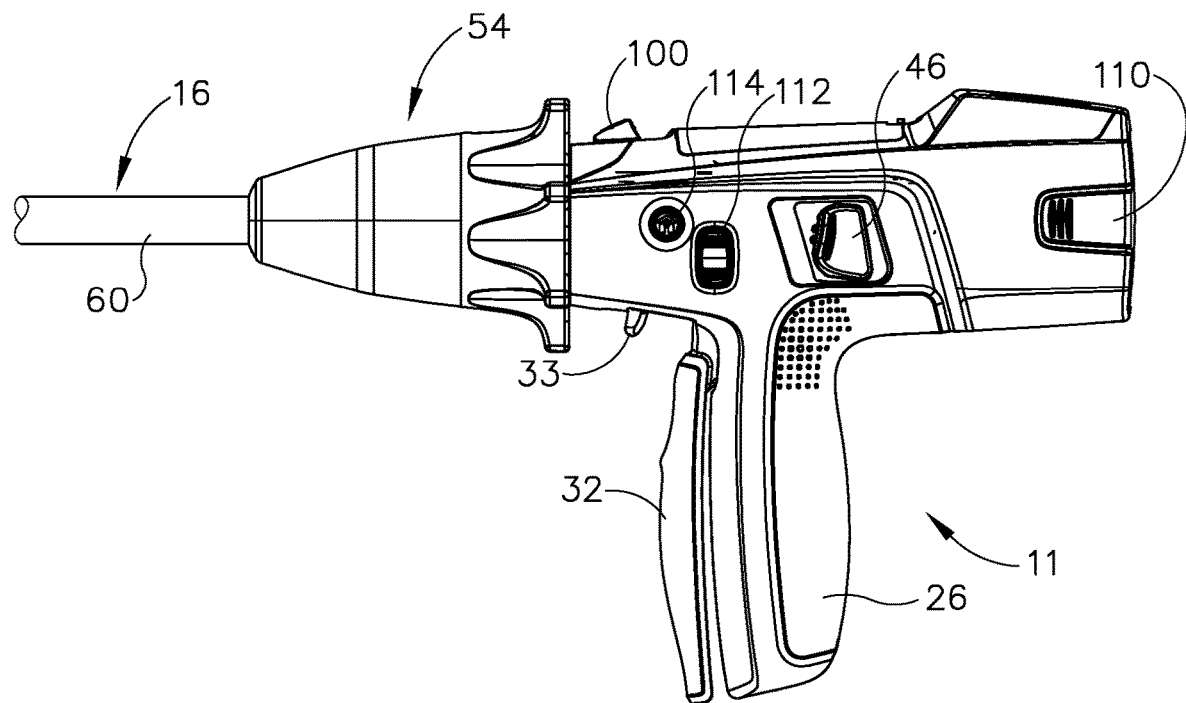
FIG. 4B depicts a side elevational view of a proximal portion of the instrument of FIG. 1, with the closure trigger in a second pivotal position and the firing trigger in a second pivotal position.
Figure 4C:
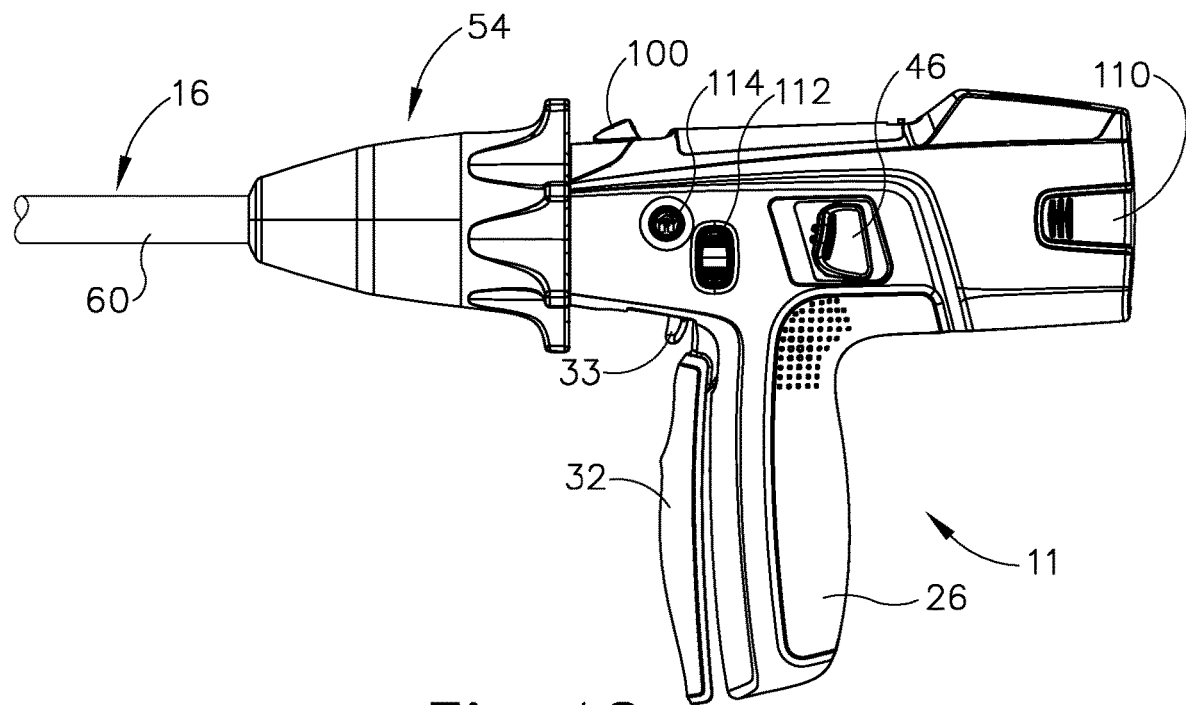
FIG. 4C depicts a side elevational view of a proximal portion of the instrument of FIG. 1, with the closure trigger in the second pivotal position and the firing trigger in a third pivotal position.

FIGS. 4A-4C show the different states of handle assembly (11) during the different states of actuation of end effector (18). In FIG. 4A, handle assembly (11) is in a state where closure trigger (32) is in a non-actuated pivotal position and firing trigger (33) is in a non-actuated pivotal position. At this stage, end effector (18) is in an opened state where anvil (50) is pivoted away from staple cartridge (20).

In FIG. 4B, handle assembly (11) is in a state where closure trigger (32) is in an actuated pivotal position. As noted above, closure trigger (32) will be locked in this position until the operator actuates release button assembly (46). At this stage, end effector is in a closed but unfired state where anvil (50) is pivoted toward staple cartridge (20), such that tissue is being compressed between anvil (50) and cartridge (20). However, firing shaft (82) has not yet been driven distally to actuate staples from staple cartridge (20), and the knife at the distal end of firing shaft (82) has not yet severed the tissue between anvil (20) and staple cartridge (20). It should be noted that firing trigger (33) is in a partially-actuated pivotal position in FIG. 4B, due to the travel of closure trigger (32) from the non-actuated pivotal position to the actuated pivotal position. However, this movement of firing trigger (33) is only provided to improve access to firing trigger (33) for the operator. In other words, this movement of firing trigger (33) from the position shown in FIG. 4A to the position shown in FIG. 4B does not yet activate a firing sequence.

In FIG. 4C, handle assembly is in a state where closure trigger (32) remains in the actuated pivotal position, and firing trigger (33) has been pivoted to an actuated pivotal position. This actuation of firing trigger (33) activates motor (118) to drive longitudinal drive member (86) longitudinally, which in turn drives firing shaft (82) longitudinally. The longitudinal movement of firing shaft (82) results in actuation of staples from staple cartridge (20) into the tissue compressed between anvil (50) and staple cartridge (20); and further results in the severing of the tissue compressed between anvil (50) and staple cartridge (20). In some versions, an additional safety trigger is provided. For instance, the additional safety trigger may prevent actuation of firing trigger (33) until the safety trigger is actuated. In other words, after reaching the state shown in FIG. 4B, when the operator is ready to actuate firing trigger (33), the operator must first actuate the safety trigger and then actuate firing trigger (33). The presence of a safety trigger may prevent inadvertent actuation of firing trigger (33).

It should also be understood that, in the present example, the actuation of anvil (50) toward staple cartridge (20) is provided through purely mechanical couplings between closure trigger (32) and anvil (50), such that motor (118) is not used to actuate anvil (50). It should also be understood that, in the present example, the actuation of firing shaft (82) (and, hence, the actuation of staple cartridge (20)) is provided through activation of motor (118). In addition, the actuation of articulation joint (52) is provided through activation of motor (118) in the present example. This motorized actuation of articulation joint (52) is provided via longitudinal translation of drive member (86). A clutch assembly (not shown) within shaft assembly (16) is operable to selectively couple longitudinal translation of drive member (86) with features to either drive articulation joint (52) or actuate staple cartridge (20). Such selective coupling via the clutch assembly is based on the pivotal position of closure trigger (32). In particular, when closure trigger (32) is in the non-actuated position shown in FIG. 4A, activation of motor (118) (in response to activation of articulation control rocker (112)) will drive articulation joint (52). When closure trigger (32) is in the actuated position shown in FIG. 4B, activation of motor (118) (in response to actuation of firing trigger (33)) will actuate staple cartridge (20). By way of example only, the clutch assembly may be configured and operable in accordance with at least some of the teachings of U.S. Pub. No. 2015/0280384, issued as U.S. Pat. No. 10,201,364, the disclosure of which is incorporated by reference herein.

In the present example, handle assembly (11) also includes a "home" button (114). By way of example only, when anvil (50) is in a closed position, "home" button (114) may be operable to activate motor (118) to retract drive member (86) proximally to a proximal-most, "home" position. In addition, or in the alternative, when anvil (50) is in an open position, "home" button (114) may be operable to activate motor (118) to drive articulation joint (52) to achieve a non-articulated state, such that end effector (18) is coaxially aligned with shaft assembly (16). In addition, or in the alternative, "home" button (114) may activate graphical user interface (116) to return to a "home" screen. Other suitable operations that may be provided in response to activation of "home" button (114) will be apparent to those of ordinary skill in the art in view of the teachings herein.

Shaft assembly (16) of the present example further includes a latch system for removably coupling shaft assembly (16) to handle assembly (11) and, more specifically, to frame (28). By way of example only, this latch system may include a lock yoke or other kind of lock member that is movably coupled to chassis (64). As shown in FIG. 3, such a lock yoke may include two proximally protruding lock lugs (96) that are configured for releasable engagement with corresponding lock detents or grooves (98) in frame (28). In some versions, the lock yoke is biased in the proximal direction by a resilient member (e.g., a spring, etc.). Actuation of the lock yoke may be accomplished by a latch button (100) that is slidably mounted on a latch actuator assembly (102) that is mounted to chassis (64). Latch button (100) may be biased in a proximal direction relative to the lock yoke. The lock yoke may be moved to an unlocked position by urging latch button (100) the in distal direction, which also causes the lock yoke to pivot out of retaining engagement with frame (28). When the lock yoke is in "retaining engagement" with frame (28), lock lugs (96) are retainingly seated within the corresponding lock detents or grooves (98). By way of further example only, shaft assembly (16) may be removably coupled with handle assembly (11) in accordance with at least some of the teachings of U.S. Pub. No. 2017/0086823, entitled "Surgical Stapling Instrument with Shaft Release, Powered Firing, and Powered Articulation," published Mar. 30, 2017, issued as U.S. Pat. No. 10,182,813 on Jan. 22, 2019, the disclosure of which is incorporated by reference herein; in accordance with at least some of the teachings of U.S. Pub. No. 2015/0280384, issued as U.S. Pat. No. 10,201,364, the disclosure of which is incorporated by reference herein; and/or in any other suitable fashion.

To commence the coupling process between shaft assembly (16) and handle assembly (11), the clinician may position chassis (64) of interchangeable shaft assembly (16) above or adjacent to frame (28) such that tapered attachment portions (74) formed on chassis (64) are aligned with dovetail slots (76) in frame (28). The clinician may then move shaft assembly (16) along an installation axis (IA) that is perpendicular to the longitudinal axis of shaft assembly (16) to seat attachment portions (74) in "operative engagement" with the corresponding dovetail receiving slots (76). In doing so, shaft attachment lug (80) on intermediate firing shaft (82) will also be seated in cradle (84) in the longitudinally movable drive member (86) and the portions of pin (42) on second closure link (38) will be seated in the corresponding hooks (66) in closure shuttle (62). As used herein, the term "operative engagement" in the context of two components means that the two components are sufficiently engaged with each other so that upon application of an actuation motion thereto, the components may carry out their intended action, function, and/or procedure.

As discussed above, at least five systems of interchangeable shaft assembly (16) may be operatively coupled with at least five corresponding systems of handle (14). A first system comprises a frame system that couples and/or aligns the frame or spine of shaft assembly (16) with frame (28) of the handle (14). A second system is the latch system that releasably locks the shaft assembly (16) to the handle (14).

A third system is closure drive system (30) that may operatively connect closure trigger (32) of handle (14) and closure tube (60) and anvil (50) of shaft assembly (16). As outlined above, closure shuttle (62) of shaft assembly (16) engages with pin (42) on second closure link (38). Through closure drive system (30), anvil (50) pivots toward and away from staple cartridge (20) based on pivotal movement of closure trigger (32) toward and away from pistol grip (26).

A fourth system is an articulation and firing drive system operatively connecting firing trigger (33) of handle (14) with intermediate firing shaft (82) of the shaft assembly (16). As outlined above, the shaft attachment lug (80) operatively connects with the cradle (84) of the longitudinal drive member (86). This fourth system provides motorized actuation of either articulation joint (52) or staple cartridge (20), depending on the pivotal position of closure trigger (32). When closure trigger (32) is in a non-actuated pivotal position, the fourth system operatively connects articulation control rocker (112) with articulation joint (52), thereby providing motorized pivotal deflection of end effector (18) toward and away from the longitudinal axis of shaft assembly (11) at articulation joint (52). When closure trigger (32) is in an actuated pivotal position, the fourth system operatively connects firing trigger (33) with staple cartridge (20), resulting in stapling and cutting of tissue captured between anvil (50) and staple cartridge (20) in response to actuation of firing trigger (33).

A fifth system is an electrical system that can signal to control circuit (117) in handle (14) that the shaft assembly (16) has been operatively engaged with the handle (14), to conduct power and/or communicate signals between the shaft assembly (16) and the handle (14). In the present example, and as shown in FIG. 3, shaft assembly (16) includes an electrical connector (106) that is operatively mounted to a shaft circuit board (not shown). Electrical connector (106) is configured for mating engagement with a corresponding electrical connector (108) on a handle control board (not shown). Further details regarding the circuitry and control systems may be found in U.S. Pub. No. 2014/0263541, now abandoned, the disclosure of which is incorporated by reference herein and/or U.S. Pub. No. 2015/0272575, issued as U.S. Pat. No. 9,913,642, the disclosure of which is incorporated by reference herein.

Other kinds of systems of interchangeable shaft assembly (16) that may be operatively coupled with at corresponding systems of the handle (14) will be apparent to those of ordinary skill in the art in view of the teachings herein.

As noted above, handle assembly (11) of the present example includes a graphical user interface (116). By way of example only, graphical user interface (116) may be used to display various information about the operational state of battery (110), the operational state of end effector (18), the operational state of articulation joint (52), the operational state of triggers (32, 33), and/or any other kinds of information. Other suitable kinds of information that may be displayed via graphical user interface will be apparent to those of ordinary skill in the art in view of the teachings herein.

Figure 6:
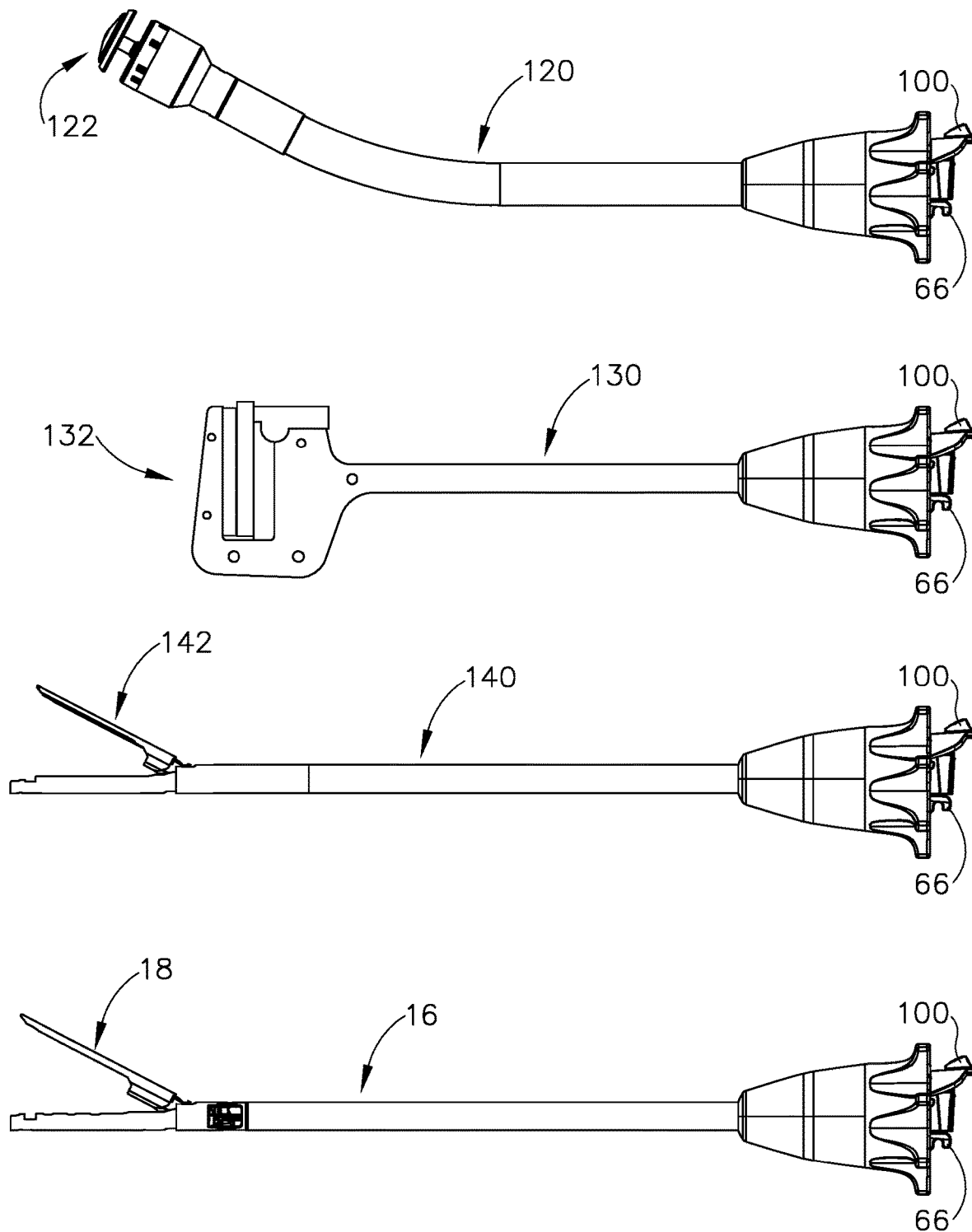
FIG. 6 depicts a side elevational view of an array of alternative shaft assemblies that may be used with the instrument of FIG. 1.

Handle assembly (11) may be configured for use with interchangeable shaft assemblies that include end effectors that are adapted to support different sizes and types of staple cartridges, have different shaft lengths, sizes, and types, etc. By way of example only, FIG. 6 shows various kinds of shaft assemblies (16, 120, 130, 140) that may be used with handle assembly (11). In particular, FIG. 6 shows a circular stapler shaft assembly (120) with an end effector (122) that is operable to perform a circular stapling and cutting operation (e.g., end-to-end anastomosis); a liner stapler shaft assembly (130) with an end effector (132) that is operable to perform a linear stapling operation; and a second endocutter shaft assembly (140) with an end effector (142) that is operable to perform the same kind of stapling and cutting operation as end effector (18). However, in this example, shaft assembly (140) is shorter than shaft assembly (16), shaft assembly (140) has a smaller diameter than shaft assembly (16), and end effector (142) is smaller than end effector (18). It should be understood that these various surgical stapling shaft assemblies (16, 120, 130, 140) are merely illustrative examples.

It should also be understood that control circuit (117) may be configured to detect the kind of shaft assembly (16, 120, 130, 140) coupled with handle assembly (11), and select a control algorithm suited for that kind of shaft assembly (16, 120, 130, 140). As another merely illustrative example, each shaft assembly (16, 120, 130, 140) may have a chip or other memory device storing the control algorithm suited for that kind of shaft assembly (16, 120, 130, 140); and control circuit (117) may receive and execute that control algorithm after shaft assembly (16, 120, 130, 140) is coupled with handle assembly (11).

In addition, handle assembly (11) may also be effectively employed with a variety of other interchangeable shaft assemblies including those assemblies that are configured to apply other motions and kinds of energy such as, for example, radio frequency (RF) energy, ultrasonic energy and/or motion to end effector arrangements adapted for use with various surgical applications and procedures. Furthermore, end effectors, shaft assemblies, handles, surgical instruments, and/or surgical instrument systems can utilize any suitable fastener, or fasteners, to fasten tissue. For instance, a fastener cartridge comprising a plurality of fasteners removably stored therein can be removably inserted into and/or attached to the end effector of a shaft assembly. Various examples of such cartridges are disclosed in various references that are cited herein.

The various shaft assemblies (16) disclosed herein may employ sensors and various other components that require electrical communication with control circuit (117) in handled assembly (11). The electrical communications may be provided via mating electrical connectors (106, 108). By way of example only, such sensors and other components may be constructed and operable in accordance with at least some of the teachings of U.S. Pub. No. 2015/0272575, issued as U.S. Pat. No. 9,913,642, the disclosure of which is incorporated by reference herein. In addition, or in the alternative, instrument (10) may be constructed and operable in accordance with at least some of the teachings of any of the various other references that are cited herein.

It will be appreciated that the various teachings herein may also be effectively employed in connection with robotically-controlled surgical systems. Thus, the term "housing" or "body" may also encompass a housing, body, or similar portion of a robotic system that houses or otherwise operatively supports at least one drive system that is configured to generate and apply at least one control motion which could be used to actuate the interchangeable shaft assemblies disclosed herein and their respective equivalents. The term "frame" may refer to a portion of a handheld surgical instrument. The term "frame" may also represent a portion of a robotically controlled surgical instrument and/or a portion of the robotic system that may be used to operatively control a surgical instrument. By way of example only, the interchangeable shaft assemblies disclosed herein may be employed with any of the various robotic systems, instruments, components and methods disclosed in U.S. Pat. No. 9,072,535, entitled "Surgical Stapling Instruments with Rotatable Staple Deployment Arrangements," issued Jul. 7, 2015, the disclosure of which is incorporated by reference herein.

II. EXEMPLARY SURGICAL INSTRUMENT WITH ROTARY DRIVE ASSEMBLY

Instrument (10) of the example described above provides linearly actuated drive features coupling handle assembly (11) with shaft assembly (16, 120, 130, 140), including firing shaft (80) coupled with longitudinal drive member (86) and hooks (66) coupled with closure link (38), such that linear motion of these coupling drive features is required to operate instrument (10). Some other instruments may provide angularly actuated coupling features, such that rotary motion of the coupling drive features is required to operate the instrument.

Figure 7:
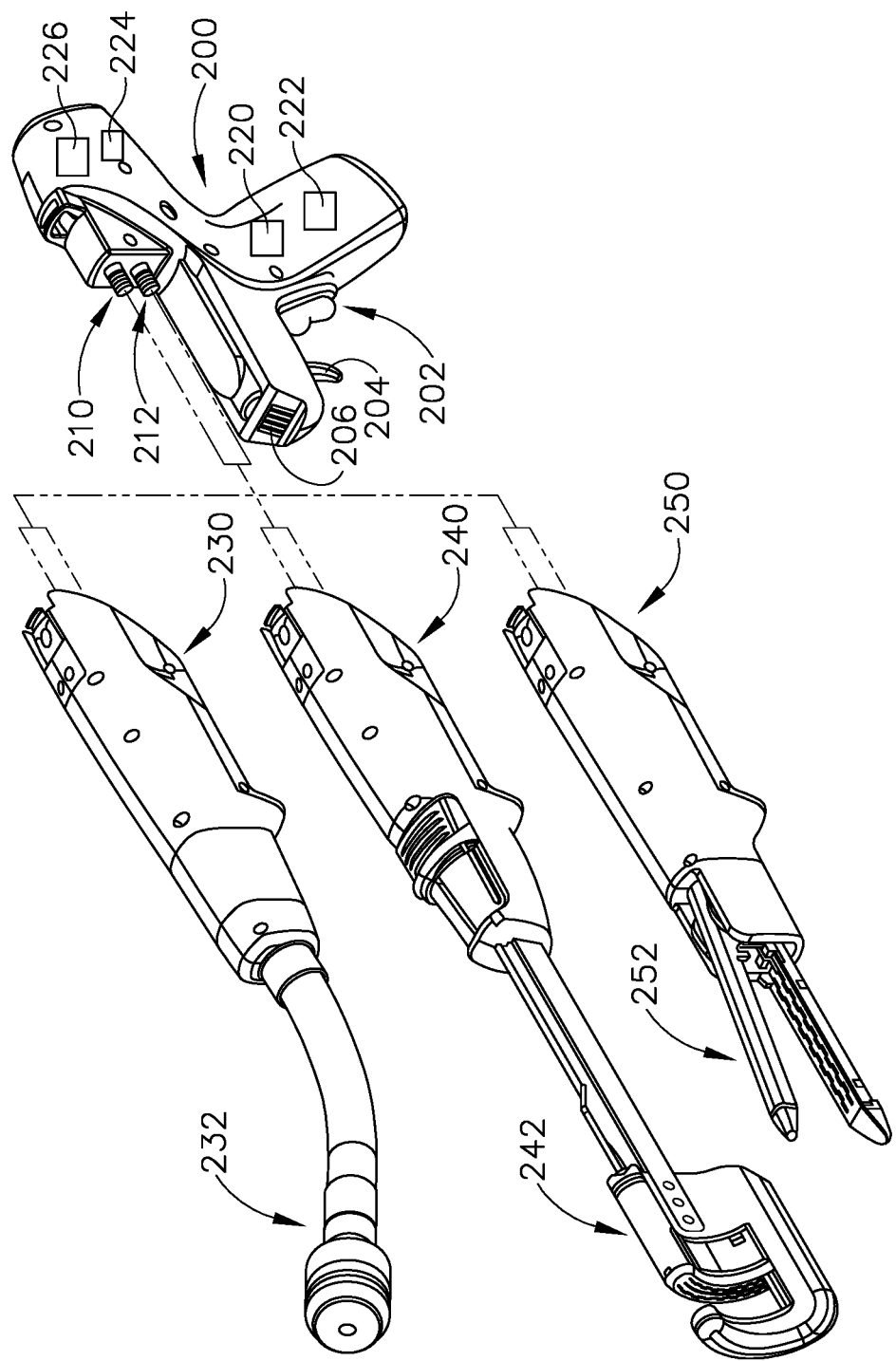
FIG. 7 depicts a perspective view of an exemplary alternative handle assembly and an array of associated alternative shaft assemblies.

FIG. 7 shows an example of an instrument that relies on rotation of drive features coupling a handle assembly (200) with a selected shaft assembly (230, 240, 250) to actuate the instrument that is formed by coupling handle assembly (200) with a selected shaft assembly (230, 240, 250). Handle assembly (200) of this example comprises a first trigger (202), a second trigger (204), an electrical connector (206), a first rotary driver (210), and a second rotary driver (212).

Handle assembly (200) further includes a control module (220), an internal power source (222) (e.g., a battery), a first motor (224), and a second motor (224). Control module (220) is configured to process signals that are received through and/or sent through electrical connector (206). Control module (220) is also configured to respond to signals generated by manual actuation of triggers (202, 204). In particular, control module (220) is configured to direct power from power source (222) to one or both of motors (224, 226) in accordance with one or more control algorithms. Such control algorithms may vary based on input from triggers (202, 204) and based on signals received via electrical connector (206). When motor (226) is activated by control module (220), motor (226) drives rotary driver (210) to rotate. When motor (226) is activated by control module (220), motor (226) drives rotary driver (210) to rotate.

The proximal end of each shaft assembly (230, 240, 250) is configured to removably couple with handle assembly (200) to form an assembled instrument. The proximal end of each shaft assembly (230, 240, 250) includes a pair of rotary inputs that are configured to couple with respective rotary drivers (210, 212). Each shaft assembly (230, 240, 250) includes a respective end effector (232, 242, 252) that is actuated by rotation of the rotary inputs from rotary drivers (210, 212). End effector (232) of shaft assembly (230) is like end effector (122) and is operable to perform a circular stapling and cutting operation (e.g., end-to-end anastomosis). End effector (242) of shaft assembly (240) is operable to perform a curvilinear stapling and cutting operation (e.g., a lower anterior resection of the bowel). End effector (252) of shaft assembly (250) is operable to perform a linear stapling operation. In some versions, rotation of one rotary driver (210, 212) causes the coupled end effector (232, 242, 252) to compress tissue; while rotation of the other rotary driver (210, 212) causes the coupled end effector (232, 242, 252) to sever and staple the compressed tissue. Various suitable ways in which rotary drivers (210, 212) may be coupled with end effectors (232, 242, 252) will be apparent to those of ordinary skill in the art in view of the teachings herein.

In addition to the foregoing, handle assembly (200) and each shaft assembly (230, 240, 250) may be further configured and operable in accordance with at least some of the teachings of U.S. Pub. No. 2016/0249917, entitled "Surgical Apparatus Configured to Track an End-of-Life Parameter," published Sep. 1, 2016, issued as U.S. Pat. No. 10,159,483 on Dec. 25, 2018, the disclosure of which is incorporated by reference herein. Handle assembly (200) and shaft assemblies (230, 240, 250) are described herein only to illustrate examples of instrumentation where rotary motion of coupling drive features is required to operate the instrument. Other kinds of instrumentation where modular handle and shaft assemblies removably couple via one or more rotary drive features will be apparent to those of ordinary skill in the art in view of the teachings herein.

III. EXEMPLARY HANDLE ASSEMBLY WITH DUAL-DRIVE CAPABILITY

A. Overview

As described above, some shaft assemblies (16, 120, 130, 140) are configured to provide actuation of an end effector (18, 122, 132, 142) in response to linear movement of features coupling shaft assembly (16, 120, 130, 140) with a handle assembly (12). Other shaft assemblies (230, 240, 250) are configured to provide actuation of an end effector (232, 242, 252) in response to rotary movement of features coupling shaft assembly (230, 240, 250) with a handle assembly (200).

It may be desirable to provide a modified version of handle assemblies (12, 200) where the modified handle assembly is capable of operably coupling with linearly driven shaft assemblies (16, 120, 130, 140) and with rotationally driven shaft assemblies (230, 240, 250). Such a "universal" handle assembly may reduce the need for having two different kinds of handle assemblies to operate a wide array of shaft assemblies (16, 120, 130, 140, 230, 240, 250). Such a universal handle assembly may also have sensing capabilities that enable the handle assembly to determine whether the coupled shaft assembly (16, 120, 130, 140, 230, 240, 250) requires a linear drive input, a rotary drive input, or a combination of linear and rotary drive inputs; and provide the required kind(s) of input accordingly. The following description provides several merely illustrative examples of universal handle assemblies that are capable of providing a linear drive output, a rotary drive output, or a combination of linear and rotary drive output. Other examples will be apparent to those of ordinary skill in the art in view of the teachings herein.

Figure 8:
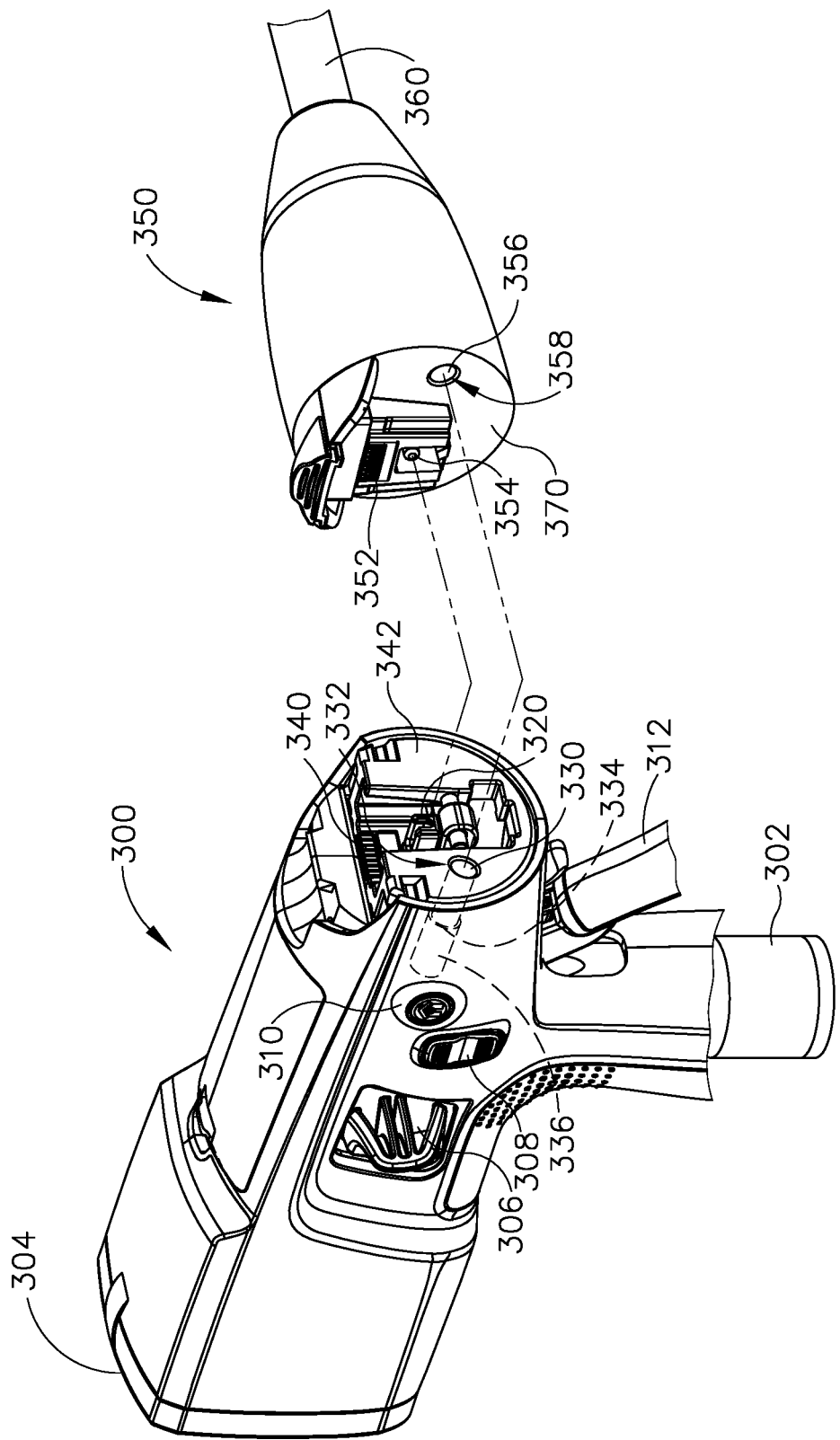
FIG. 8 depicts depicts a perspective view of a portion of an exemplary alternative shaft assembly separated from a portion of an exemplary alternative dual-drive handle assembly.

FIG. 8 shows an exemplary handle assembly (300) and an exemplary shaft assembly (350). Handle assembly (300) of this example comprises a primary motor (302), a flip-up screen (304), a closure release assembly (306), an articulation control rocker (308), a "home" button (310), a closure trigger (312), a firing shaft attachment cradle (320), a secondary motor (336), and an electrical connector (340). While not shown, handle assembly (300) also includes an integral power source (e.g., battery, etc.) and a control module. The control module is in communication with the integral power source, motors (302, 336), and electrical connector (340). Primary motor (302) is coupled with firing shaft attachment cradle (320) and is operable to drive firing shaft attachment cradle (320) linearly. By way of example only, a rack and pinion assembly (not shown) and/or any other suitable kind of mechanical transmission assembly may be used to convert rotary motion from primary motor (302) into linear movement of firing shaft attachment cradle (320). The coupling between motor (302) and firing shaft attachment cradle (320) may be the same as the coupling between motor (118) and firing shaft attachment cradle (86) described above.

Flip-up screen (304) is operable to provide a graphical user interface displaying information relating to handle assembly (300) and operation of handle assembly (300). Flip-up screen (304) may be configured and operable just like graphical user interface (116) described above. Flip-up screen (304) may be further configured and operable for repositioning in accordance with at least some of the teachings of U.S. patent application Ser. No. 15/634,418, entitled "Surgical Instrument with Integrated and Independently Powered Displays," filed on Jun. 27, 2017, issued as U.S. Pat. No. 10,163,309 on Dec. 25, 2018, the disclosure of which is incorporated by reference herein.

Closure release assembly (306), articulation control rocker (308), "home" button (310), closure trigger (312), and firing shaft attachment cradle (320) may be configured and operable just like closure release assembly (44), articulation control rocker (112), "home" button (114), closure trigger (32), and firing shaft attachment cradle (84), respectively, as described above. While not shown in FIG. 8, handle assembly (300) may also include a firing trigger just like firing trigger (33); and other components like those of handle assembly (12).

Figure 9A:
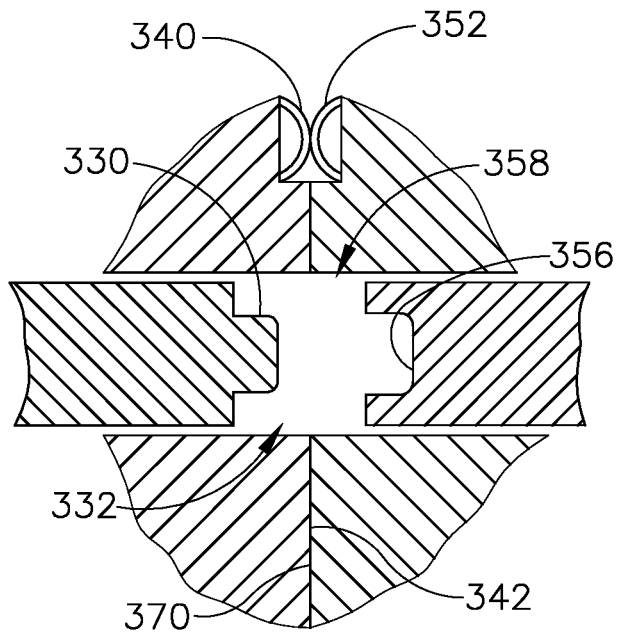
FIG. 9A depicts a partial cross-sectional side view of the handle assembly of FIG. 8 coupled with the shaft assembly of FIG. 8, with a rotary drive member of the handle assembly of FIG. 8 disengaged from a corresponding rotary driven member of the shaft assembly of FIG. 8.
Figure 9B:
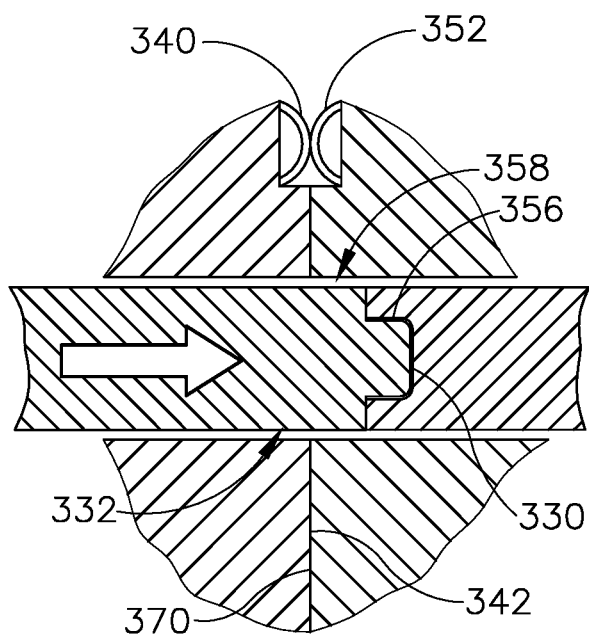
FIG. 9B depicts a partial cross-sectional side view of the handle assembly of FIG. 8 coupled with the shaft assembly of FIG. 8, with the rotary drive member of the handle assembly of FIG. 8 engaged with the corresponding rotary driven member of the shaft assembly of FIG. 8.

Handle assembly (300) of the present example further includes a rotary drive spindle (330) and a clutch (334) that is operable to transition rotary drive spindle (330) between a proximal position (FIG. 9A) and a distal position (FIG. 9B). By way of example only, clutch (334) may comprise a solenoid or any other suitable kind of device or assembly that is operable to transition rotary drive spindle (330) between a proximal position (FIG. 9A) and a distal position (FIG. 9B) while enabling spindle (330) to communicate rotary motion from secondary motor (336) when spindle (330) is in the distal position.

Shaft assembly (350) of this example comprises an electrical connector (352), a firing shaft (354), a rotary drive spindle (356), and a shaft (360). The distal end of shaft (360) may include any suitable kind of end effector (not shown), including but not limited to any of the various end effectors (18, 122, 132, 142, 252, 242, 252) described above. Shaft assembly (350) is configured such that a portion of the end effector at the distal end of shaft (360) is controlled through linear translation of firing shaft (354); and another portion of the end effector at the distal end of shaft (360) is controlled through rotation of rotary drive spindle (356). Various suitable ways in which an end effector at the distal end of shaft (360) may be driven by linear translation of firing shaft (354) and/or rotation of rotary drive spindle (356) will be apparent to those of ordinary skill in the art in view of the teachings herein.

Handle assembly (300) is configured to removably couple with shaft assembly (350), in a manner like the manner in which handle assembly (12) couples with shaft assemblies (16, 120, 130, 140). As shown in FIGS. 9A-9B, when handle assembly (300) is coupled with shaft assembly (350), electrical connectors (340, 352) contact each other, thereby providing paths for electrical communication between handle assembly (300) and shaft assembly (350). In addition, a proximally facing surface (370) of shaft assembly (350) abuts a distally facing surface (342) of handle assembly (300).

As also shown in FIGS. 9A-9B, rotary drive spindle (330) is disposed in an opening (332) formed through distally facing surface (342) of handle assembly (300); while rotary drive spindle (356) is disposed in an opening (358) formed through proximally facing surface (370) of shaft assembly (350). The proximal end of rotary drive spindle (356) is recessed relative to proximally facing surface (370) of shaft assembly (350). When rotary drive spindle (330) is in the proximal position (FIG. 9A), rotary drive spindle (330) is recessed relative to distally facing surface (342) of handle assembly (300). However, when rotary drive spindle (330) is in the distal position (FIG. 9B), rotary drive spindle (330) protrudes relative to distally facing surface (342) of handle assembly (300) to couple with rotary drive spindle (356) of shaft assembly (350). When rotary drive spindles (330, 356) are coupled together, rotary drive spindle (330) is operable to impart rotation to rotary drive spindle (356). Secondary motor (336) is operable to thereby rotationally drive associated components in shaft assembly (350).

A control module (not shown) in handle assembly (300) is configured to activate clutch (334), to thereby transition rotary drive spindle (330) between the distal position and the proximal position, based on a signal indicating whether the shaft assembly that is coupled with handle assembly (300) requires a rotary drive input. Thus, when the control module detects the presence of a coupled shaft assembly that requires a rotary drive input, the control module activates clutch (334) to drive rotary drive spindle (330) to the distal position. When the control module detects the presence of a coupled shaft assembly that does not require a rotary drive input, clutch (334) will remain inactivated and rotary drive spindle (330) will remain in the proximal position. Thus, in the present example, rotary drive spindle (330) will remain in the proximal position by default; and will only be driven to the distal position in response to a signal indicating that a rotary input is needed for a shaft assembly that is coupled with handle assembly (300).

By way of example only, the control module in handle assembly (300) may determine whether the shaft assembly that is coupled with handle assembly (300) requires a rotary input based on the presence or absence of a chip (e.g., RFID, EAS, NFC, etc.), optical code, physical protrusion, and/or other identifying feature located at the proximal end of the shaft assembly. Thus, the distal end of handle assembly (300) may include a sensor or reader that is configured to detect the presence or absence of such an identifying feature at the proximal end of the shaft assembly. As another merely illustrative example, electrical connector (352) of shaft assembly (350) may include a simple jumper feature that provides a conductive bridge between two contacts of electrical connector (340) of handle assembly (300), such that clutch (334) is activated when those two contacts of electrical connector (340) are coupled by the jumper feature of electrical connector (352). Other suitable ways in which a component of handle assembly (300) may determine whether a rotary drive input is required by a shaft assembly that is coupled with handle assembly (300) will be apparent to those of ordinary skill in the art in view of the teachings herein. Similar features and techniques may be used to enable handle assembly (300) to determine whether a linear drive input is required by a shaft assembly that is coupled with handle assembly (300).

In situations where a shaft assembly that is coupled with handle assembly (300) does not require a rotary drive input, rotary drive spindle (330) will remain in the proximal position, recessed within opening (332), as shown in FIG. 9A. In this position, rotary drive spindle (330) will not interfere with any features of the shaft assembly that is coupled with handle assembly (300). In some other variations, such as those where clutch (334) is omitted and rotary drive spindle (330) remains in the distal position shown in FIG. 9B, a shaft assembly that does not require a rotary drive input may have a recess or opening formed where rotary drive spindle (330) is located, such that the recess or opening of the shaft assembly idly receives rotary drive spindle (330) and rotary drive spindle (330) does not interfere with coupling of the shaft assembly to handle assembly (300). In situations where a shaft assembly that is coupled with handle assembly (300) does not require a linear drive input, firing shaft attachment cradle (320) may be configured to retract within a recess or opening of handle assembly (300) such that firing shaft attachment cradle (320) does not interfere with coupling of the shaft assembly to handle assembly (300). Alternatively, a shaft assembly that does not require a linear drive input may have a recess or opening formed where firing shaft attachment cradle (320) is located, such that the recess or opening of the shaft assembly idly receives firing shaft attachment cradle (320).

While handle assembly (300) of the foregoing example provides only one linear drive output (in the form of firing shaft attachment cradle (320)) and only one rotary drive output (in the form of rotary drive spindle (330)), other variations of handle assembly (300) may provide more than one linear drive output and/or more than one rotary drive output.

Figure 10:
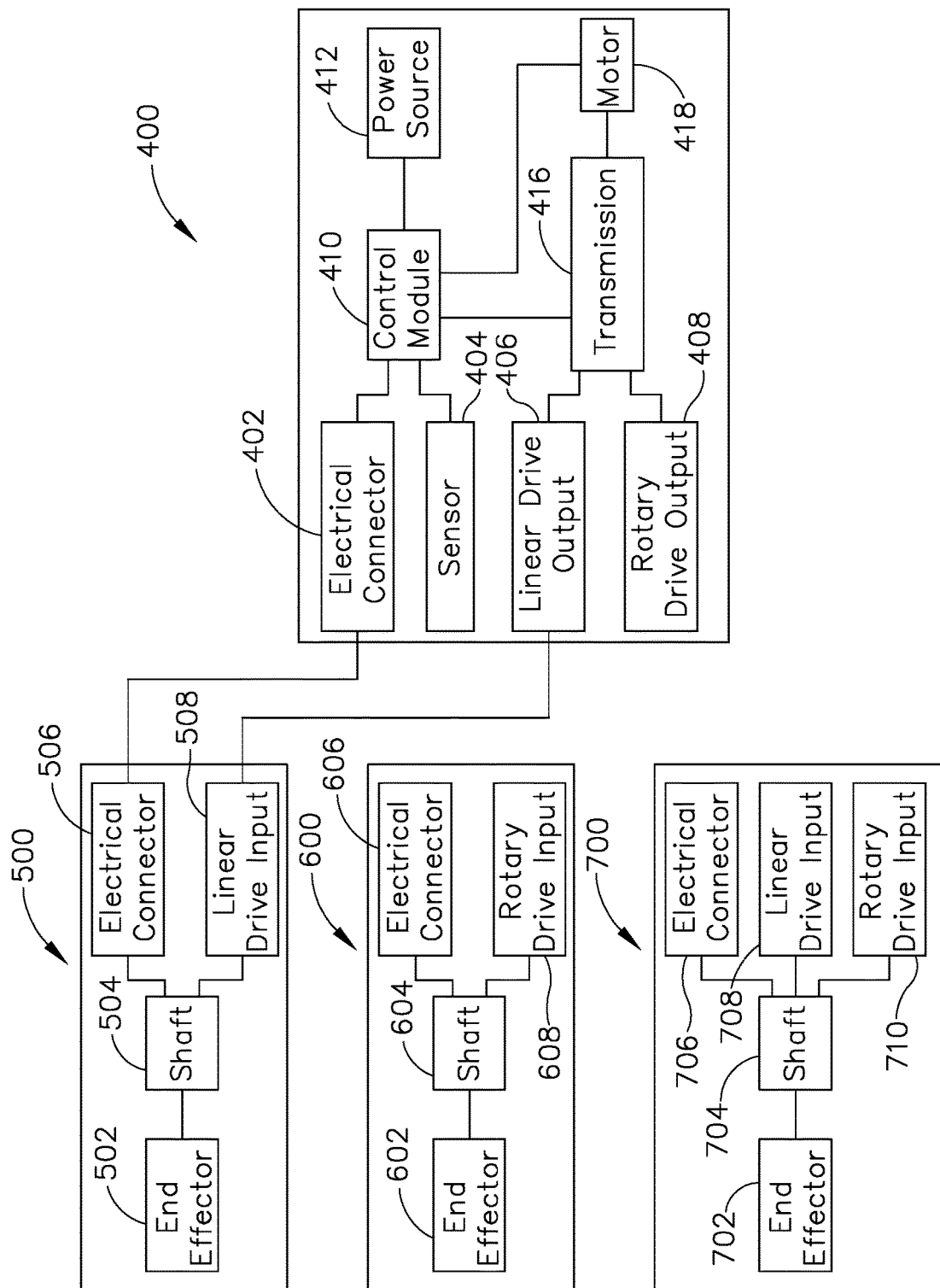
FIG. 10 depicts a schematic view of another exemplary dual-drive handle assembly coupled with a shaft assembly having a linear drive input.
Figure 11:
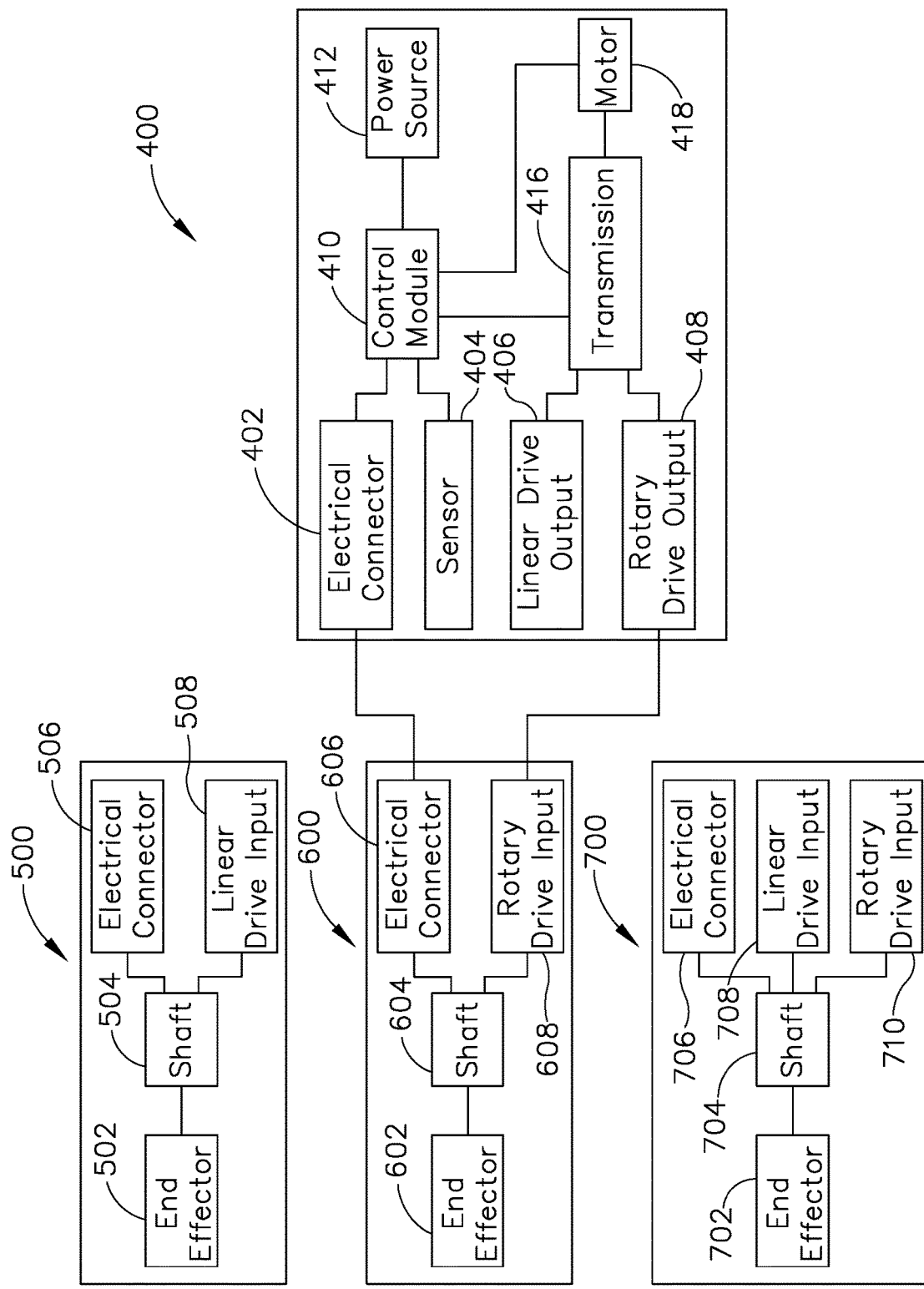
FIG. 11 depicts a schematic view of the handle assembly of FIG. 10 coupled with a shaft assembly having a rotary drive input.
Figure 12:
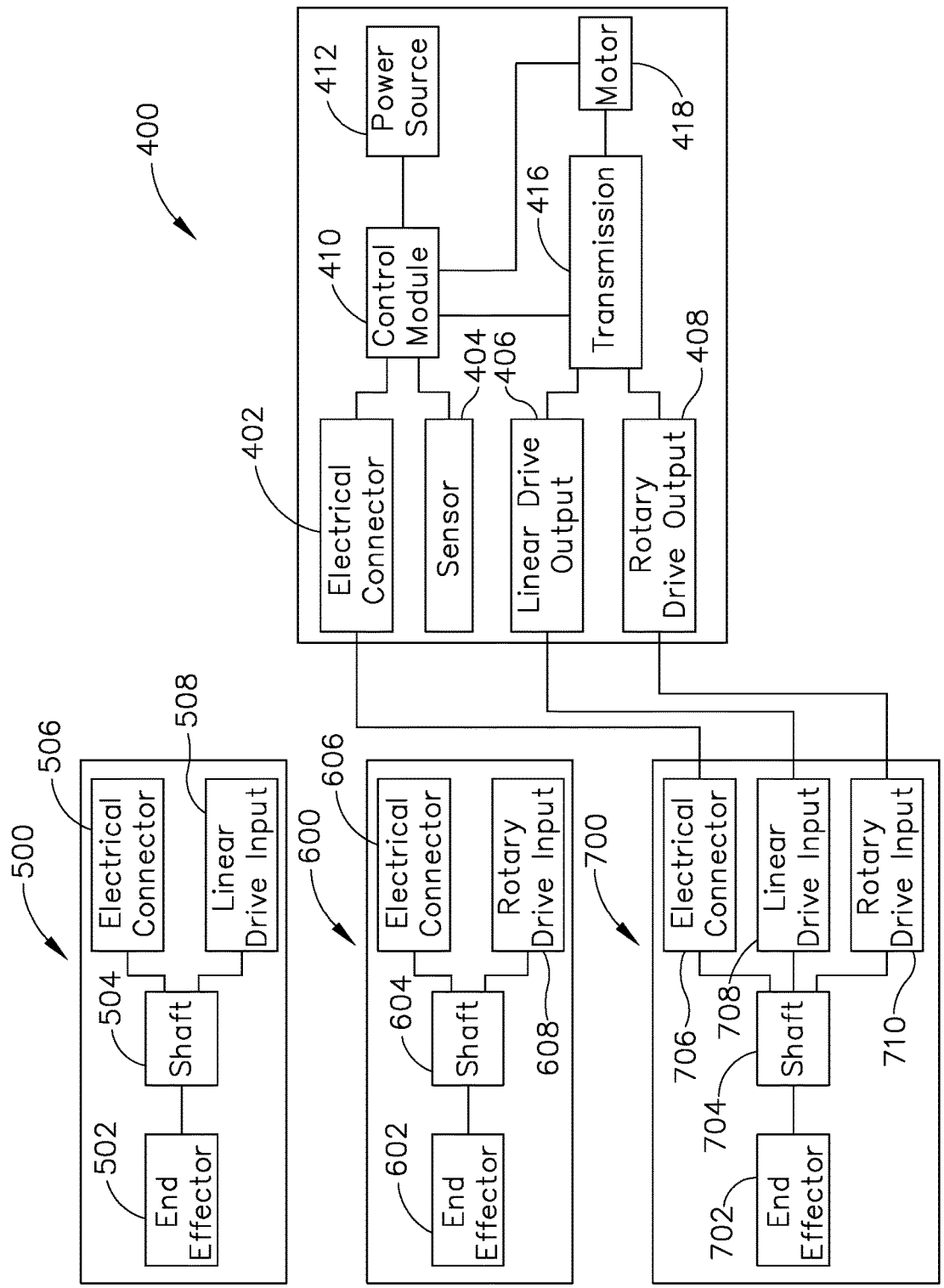
FIG. 12 depicts a schematic view of the handle assembly of FIG. 10 coupled with a shaft assembly having a linear drive input and a rotary drive input.

B. Exemplary Handle Assembly with Single Motor and Transmission to Provide Linear Drive Output and Rotary Drive Output In some instances, it may be desirable to provide a variation of handle assembly (300) that has just one single source of driving motion, with a drive assembly that is operable to convert motion from that single source into at least two different kinds of motion (e.g., linear and rotary). FIGS. 10-12 shown an example of such a variation. In particular, FIGS. 10-12 show an exemplary handle assembly (400) that comprises an electrical connector (402), a sensor (404), a linear drive output (406), a rotary drive output (408), a control module (410), a power source (412), a transmission (416), and a motor (418). Except as otherwise described below, handle assembly (400) may be at least partially configured and operable just like handle assemblies (12, 200, 300) described above. As also shown in FIGS. 10-12, handle assembly (400) may be selectively coupled with various kinds of shaft assemblies (500, 600, 700), the details of which will be described further below.

Control module (410) is in communication with electrical connector (402), sensor (404), power source (412), transmission (416), and motor (418). Control module (410) is configured to execute control algorithms to provide the functionality described below. By way of example only, control module (410) may comprise a circuit board, a microprocessor, a memory (e.g., EEPROM, etc.), and/or various other components. Various suitable ways in which control module (410) may be configured will be apparent to those of ordinary skill in the art in view of the teachings herein. Electrical connector (402) may be configured and operable like electrical connectors (108, 206, 340) described above; or may have any other suitable configuration. Sensor (404) is configured to detect the kind of shaft assembly (500, 600, 700) that is coupled with handle assembly (400). Various suitable forms that sensor (404) may take will be apparent to those of ordinary skill in the art in view of the teachings herein. Control module (410) is configured to select and execute an appropriate control algorithm based on the kind of shaft assembly (500, 600, 700) detected by sensor (404). Power source (412) may comprise one or more batteries or any other suitable kind of source of power as will be apparent to those of ordinary skill in the art in view of the teachings herein.

Motor (418) of the present example comprises a conventional motor that is operable to provide only a rotary output. In some other versions, motor (418) is operable to provide only a linear output. Various suitable forms that motor (418) may take will be apparent to those of ordinary skill in the art in view of the teachings herein. Transmission (416) is coupled with motor (418) and with drive outputs (406, 408). Continuing with the example where motor (418) provides a single rotary output, transmission (416) comprises a mechanical assembly that is operable to either pass through the rotary output of motor (418) to rotary drive output (408) (as shown in FIG. 11), convert the rotary output of motor (418) into a linear drive motion that is passed through linear drive output (406) (as shown in FIG. 10), or provide a combined rotary and linear output through outputs (406, 408) (as shown in FIG. 12). By way of example only, linear drive output (406) may be configured and operable like firing shaft attachment cradles (84, 320) as described above. Also by way of example only, rotary drive output (408) may be configured and operable like drivers (210, 212) or spindle (330) as described above. Other suitable forms that outputs (406, 408) may take will be apparent to those of ordinary skill in the art in view of the teachings herein. It should also be understand that linear drive output (406) may in fact comprise two or more linear drive outputs; and rotary drive output (408) may in fact comprise two or more rotary drive outputs.

In scenarios where transmission (416) passes through the rotary output of motor (418) to rotary drive output (408) (as shown in FIG. 11), transmission (416) may provide a gearbox and/or other assembly to affect the torque, speed, and/or other characteristics of the rotary output. In scenarios where transmission (416) converts the rotary output of motor (418) into a linear drive motion that is passed through linear drive output (406), transmission (416) may employ a rack and pinion, crankshaft, camshaft, and/or any other suitable kind(s) of component(s) to provide such conversion of motion. In scenarios where transmission (416) provides a combined rotary and linear output through outputs (406, 408), transmission (416) may be configured to provide rotary and linear outputs simultaneously. In addition, or in the alternative, in scenarios where transmission (416) provides a combined rotary and linear output through outputs (406, 408), transmission (416) may be configured to provide rotary and linear outputs separately, in a sequence or otherwise. Various suitable components and configurations that may be incorporated into transmission (416) will be apparent to those of ordinary skill in the art in view of the teachings herein.

FIG. 10 shows handle assembly (400) coupled with shaft assembly (500). Shaft assembly (500) of this example comprises an end effector (502), a shaft (504), an electrical connector (506), and a linear drive input (508). Linear drive input (508) is operable to drive end effector (502) to perform an operation on tissue (e.g., compressing the tissue, cutting the tissue, stapling the tissue, etc.). By way of example only, shaft assembly (500) may be at least partially configured and operable just like any of shaft assemblies (16, 120, 130, 140) described above. As shown in FIG. 10, when handle assembly (400) is coupled with shaft assembly (500), electrical connectors (402, 506) are coupled together, and linear drive output (406) is coupled with linear drive input (508). Sensor (404) detects the presence and type of shaft assembly (500). Control module (410) processes the corresponding data from sensor (404) and directs transmission (416) to achieve a state where motor (418) is only coupled with linear drive output (406). Motor (418) is thereby operable to drive end effector (502). Rotary drive output (408) simply remains idle.

FIG. 11 shows handle assembly (400) coupled with shaft assembly (600). Shaft assembly (600) of this example comprises an end effector (602), a shaft (604), an electrical connector (606), and a rotary drive input (608). Rotary drive input (508) is operable to drive end effector (602) to perform an operation on tissue (e.g., compressing the tissue, cutting the tissue, stapling the tissue, etc.). By way of example only, shaft assembly (600) may be at least partially configured and operable just like any of shaft assemblies (230, 240, 250) described above. As shown in FIG. 11, when handle assembly (400) is coupled with shaft assembly (600), electrical connectors (402, 606) are coupled together, and rotary drive output (408) is coupled with rotary drive input (608). Sensor (404) detects the presence and type of shaft assembly (600). Control module (410) processes the corresponding data from sensor (404) and directs transmission (416) to achieve a state where motor (418) is only coupled with rotary drive output (408). Motor (418) is thereby operable to drive end effector (602). Linear drive output (406) simply remains idle.

FIG. 12 shows handle assembly (400) coupled with shaft assembly (500). Shaft assembly (700) of this example comprises an end effector (702), a shaft (704), an electrical connector (706), a linear drive input (708), and a rotary drive input (710). Drive inputs (708, 710) are operable to drive end effector (702) to perform an operation on tissue (e.g., compressing the tissue, cutting the tissue, stapling the tissue, etc.). For instance, linear drive input (708) may be operable to drive end effector (702) to perform one particular kind of operation on tissue (e.g., compressing the tissue); while rotary drive input (710) may be operable to drive end effector (702) to perform another particular kind of operation on tissue (e.g., cutting and stapling the tissue). By way of example only, shaft assembly (700) may be at least partially configured and operable just like shaft assembly (350) described above. As shown in FIG. 12, when handle assembly (400) is coupled with shaft assembly (700), electrical connectors (402, 706) are coupled together, linear drive output (406) is coupled with linear drive input (708), and rotary drive output (408) is coupled with rotary drive input (710). Sensor (404) detects the presence and type of shaft assembly (700). Control module (410) processes the corresponding data from sensor (404) and directs transmission (416) to achieve a state where motor (418) is selectively coupled with drive outputs (406, 408). Motor (418) is thereby operable to drive end effector (702) via one or both of drive outputs (406, 408).

Figure 13:
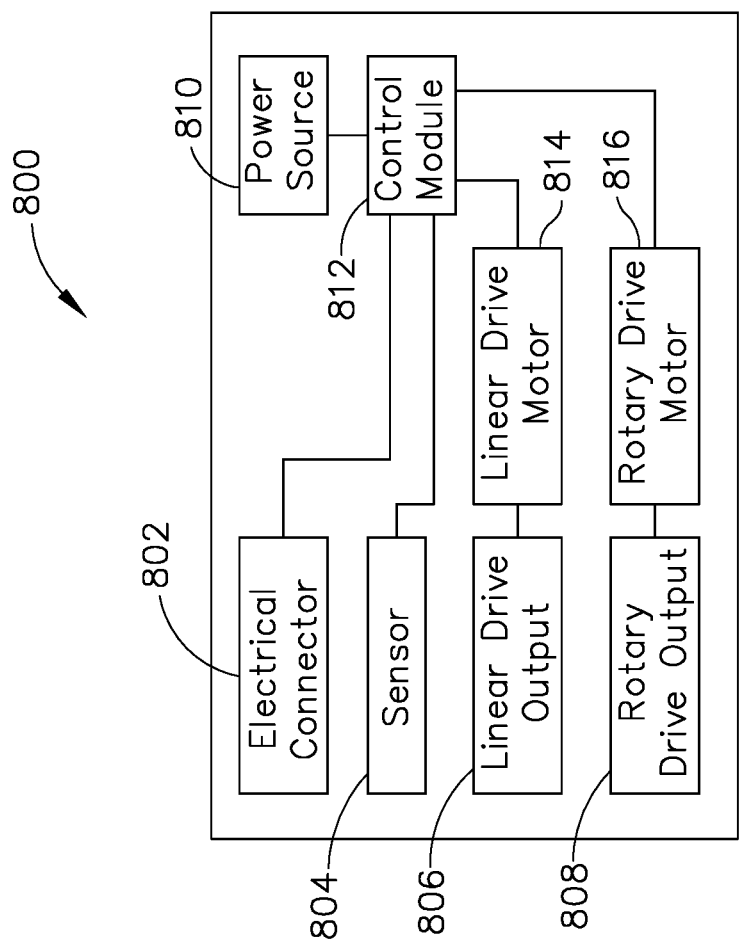
FIG. 13 depicts a schematic view of another exemplary dual-drive handle assembly.

C. Exemplary Handle Assembly with Dual Motors to Provide Linear Drive Output and Rotary Drive Output FIG. 13 shows an exemplary alternative handle assembly (800) that comprises an electrical connector (802), a sensor (804), a linear drive output (806), a rotary drive output (808), a power source (810), a control module (812), a linear drive motor (814), and a rotary drive motor (816). Electrical connector (802), sensor (804), linear drive output (806), rotary drive output (808), power source (810), and control module (812) may be configured and operable just like electrical connector (402), sensor (404), linear drive output (406), rotary drive output (408), power source (412), and control module (410) described above. Handle assembly (800) of this example may be just as compatible with shaft assemblies (500, 600, 700) as handle assembly (400).

Rather than including a single motor (418) in combination with a transmission (416) like handle assembly (400), handle assembly (800) of this example comprises separate, dedicated linear and rotary motive sources in the form of linear drive motor (814) and rotary drive motor (816). Linear drive motor (814) thus directly drives linear drive output (806) to impart linear motion to a linear drive input (508, 708) of a shaft assembly (500, 700); while rotary drive motor (814) directly drives rotary drive output (808) to impart rotary motion to a rotary drive input (608, 710) of a shaft assembly (600, 700). Linear drive motor (814) may include a linear motor, a solenoid, or some other kind of device that is configured to generate linear motion without requiring rotation of a component. Alternatively, linear drive motor (814) may comprise a rotary motor in combination with a rack and pinion, crankshaft, camshaft, and/or any other suitable kind(s) of component(s) that is/are operable to convert rotary motion into linear motion. Rotary drive motor (814) may comprise any suitable kind of conventional motor. By way of further example only, handle assembly (800) may incorporate any of the features and functionality of handle assembly (300) as described above.

When handle assembly (800) is coupled with shaft assembly (500, 600, 700), electrical connector (802) is coupled with the corresponding electrical connector (506, 606, 706). Linear drive output (806) is coupled with linear drive input (508, 708) in instances where shaft assembly (500, 700) is coupled with handle assembly (800). Rotary drive output (808) is coupled with rotary drive input (608, 710) in instances where shaft assembly (600, 700) is coupled with handle assembly (800). Sensor (804) detects the presence and type of shaft assembly (500, 600, 700). Control module (812) processes the corresponding data from sensor (804) and selectively activates linear drive motor (814) and/or rotary drive motor (816) based on the type of shaft assembly (500, 600, 700) coupled with handle assembly (800). Motors (814, 816) are thereby operable to drive end effector (502, 602, 702) via one or both of drive outputs (806, 808).

D. Exemplary User Feedback and Varied Operability Based on Modular Shaft Selection In the examples described above, handle assembly (400) provides selective activation of transmission (416) based on the type of shaft assembly (500, 600, 700) that is coupled with handle assembly (400), as sensed by sensor (404). Similarly, handle assembly (800) provides selective activation of drive motors (814, 816) based on the type of shaft assembly (500, 600, 700) that is coupled with handle assembly (800), as sensed by sensor (804).

In addition to selecting the appropriate linear or rotary drive scheme, control module (410, 812) may also initiate other kinds of responses based on the sensed type of shaft assembly (500, 600, 700). For instance, control module (410, 812) may vary the output through a user interface (e.g., graphical user interface (116), flip-up screen (304), etc.) of handle assembly (400, 800) based on the type of shaft assembly (500, 600, 700) that is coupled with handle assembly (400, 800), as sensed by sensor (404, 804). In addition, or in the alternative, control module (410, 812) may selectively enable or disable one or more user input features (e.g., closure trigger (32, 312), release button assembly (46, 306), control rocker (112, 308), "home" button (114, 318), first trigger (202), second trigger (204), etc.) of handle assembly (400, 800) based on the type of shaft assembly (500, 600, 700) that is coupled with handle assembly (400, 800), as sensed by sensor (404, 804).

In versions where control module (410, 812) selectively enables or disables one or more user input features of handle assembly (400, 800) based on the sensed type of shaft assembly (500, 600, 700), the enablement and/or disablement of user input features may be emphasized using additional user feedback. For instance, user input features that are selectively enabled based on the sensed type of shaft assembly (500, 600, 700) may be visually emphasized using illumination of the enabled user input features and/or based on a notation in a graphical user interface of handle assembly (400, 800) indicating which user input feature(s) is/are enabled. In versions where illumination is used to indicate which user input feature(s) is/are enabled, control module (419, 812) may activate such illumination selectively, based on a sequence in which the user input features are intended to be used in a surgical procedure (e.g., illuminating a tissue compression user input feature first, followed by illumination of a tissue cutting/stapling user input feature after the tissue compression user input feature is actuated). In versions where a graphical user interface is used to indicate which user input feature(s) is/are enabled, the graphical user interface may further indicate what the function is for each enabled user input feature. As another merely illustrative example, control module (410, 812) may provide haptic feedback (e.g., vibration) through handle assembly (400, 800) to indicate which user input feature(s) is/are enabled based on the sensed type of shaft assembly (500, 600, 700).

In some other variations, a removable shaft assembly (500, 600, 700) may include a feature that covers or otherwise physically obstructs one or more user input features of handle assembly (400, 800). For instance, if one version of shaft assembly (500, 600, 700) does not have a feature that is responsive to a control rocker (112, 308), that version of shaft assembly (500, 600, 700) may include a proximally extending feature that covers or otherwise obstructs control rocker (112, 308). The operator will thereby immediately understand that control rocker (112, 308) does not operate any feature of that shaft assembly (500, 600, 700).

Control module (410, 812) may also select various kinds of control algorithms for execution, based on the type of shaft assembly (500, 600, 700) that is coupled with handle assembly (400, 800), as sensed by sensor (404, 804). For instance, if shaft assembly (500, 600, 700) is a circular stapler shaft assembly (e.g., like circular stapler shaft assembly (120, 230)), control module (410, 812) may initiate an automatic draw-down or clamping sequence by automatically retracting the anvil of end effector (122, 232) when the operator actuates "home" button (114, 318). Once the anvil reaches a particular distance from a stapling deck of end effector (122, 232), control module (410, 812) may stop the proximal retraction of the anvil. Of course, this is a merely illustrative example, and other automated routines may be used. As another variation, control module (410, 812) may monitor a pressure associated with tissue compressed between the anvil and the stapling deck of end effector (122, 232), and may stop the proximal retraction of the anvil when the pressure reaches a threshold value. Even in versions where control module (410, 812) executes automated routines, control module (410, 812) may still permit manual override. For instance, control rocker (112, 308) may be used to manually adjust the longitudinal position of the anvil of end effector (122, 232).

IV. EXEMPLARY ROTARY DRIVE ASSEMBLIES

Figure 15:
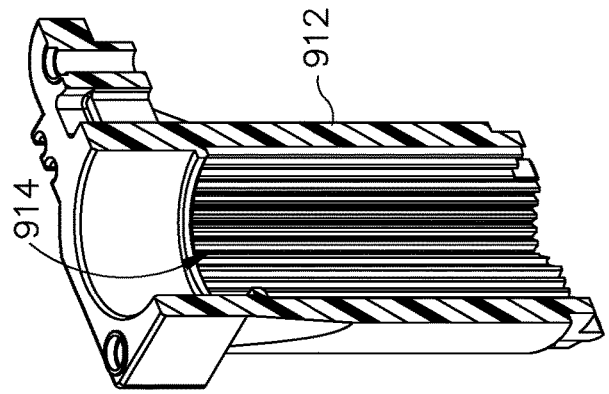
FIG. 15 depicts a cross-sectional perspective view of an outer casing of a gearbox of the rotary drive assembly of FIG. 14.
Figure 14:
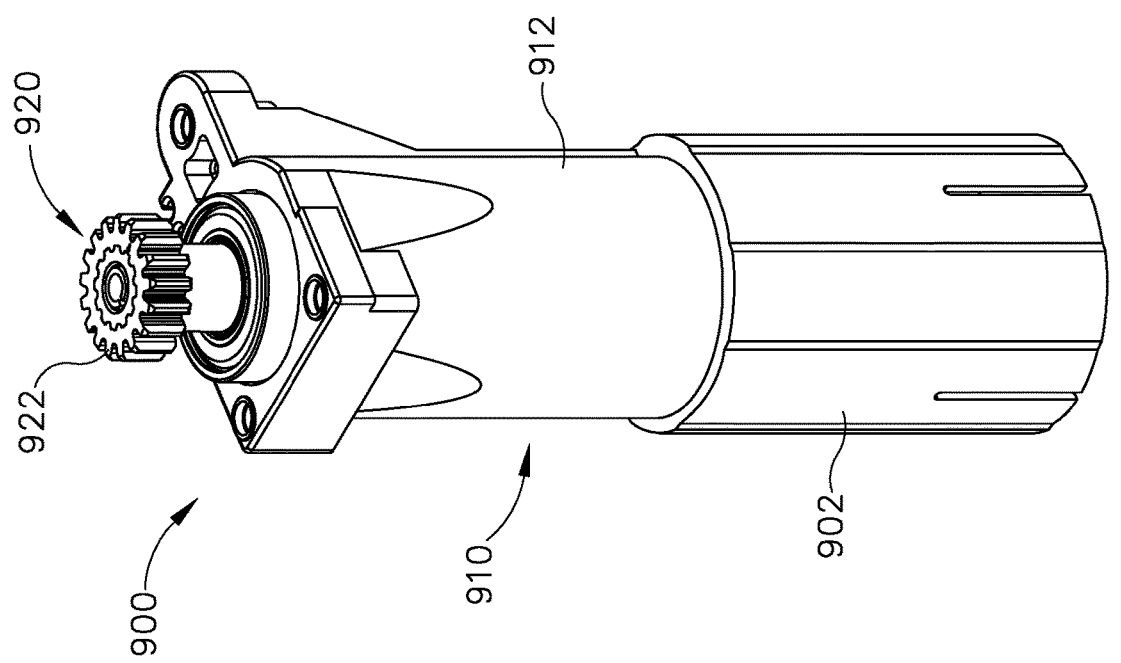
FIG. 14 depicts a perspective view of an exemplary rotary drive assembly that may be incorporated into a surgical instrument.

FIGS. 14-16 depict an exemplary rotary drive assembly (900) that may be used to drive instrument (10). Rotary drive assembly (900) may also be used to drive at least one rotary drive (210, 212), rotary drive spindle (356), rotary drive output (408, 808), or any other feature that is operable to receive a rotary drive. Rotary drive assembly (900) of this example comprises a motor (902), a gearbox assembly (910), and a driver (920). Motor (902) may comprise any suitable kind of conventional motor that is operable to provide a rotary output. Gearbox assembly (910) comprises an outer casing (912) and a set of planetary gear sets (930). As shown in FIG. 15, outer casing (912) defines a plurality of longitudinally extending teeth (914). As shown in FIG. 16, each planetary gear set (930) comprises a sun gear (932) and three planetary gears (934). Planetary gears (934) mesh with the respective sun gear (932) and teeth (914) of casing (912). Sun gears (932) are all fixedly secured to the same axle, which is directly driven by motor (902).

When motor (902) is activated to rotate sun gears (932), planetary gears (934) each rotate about their own respective axis while also orbiting about the rotation axis shared by sun gears (932). A set of drive posts (936) extend upwardly from the upper-most set of planetary gears (934). Drive posts (936) also orbit about the rotation axis shared by sun gears (932) when motor (902) is activated. Drive posts (936) are received in corresponding recesses (926) formed in a body (924) of driver (920). Due to this engagement between drive posts (936) and recesses (926), driver (920) will rotate in response to activation of motor (902). A pinion (922) of driver (920) may engage a rack, another gear, or some other component in order to drive motion as described above.

Figure 19:
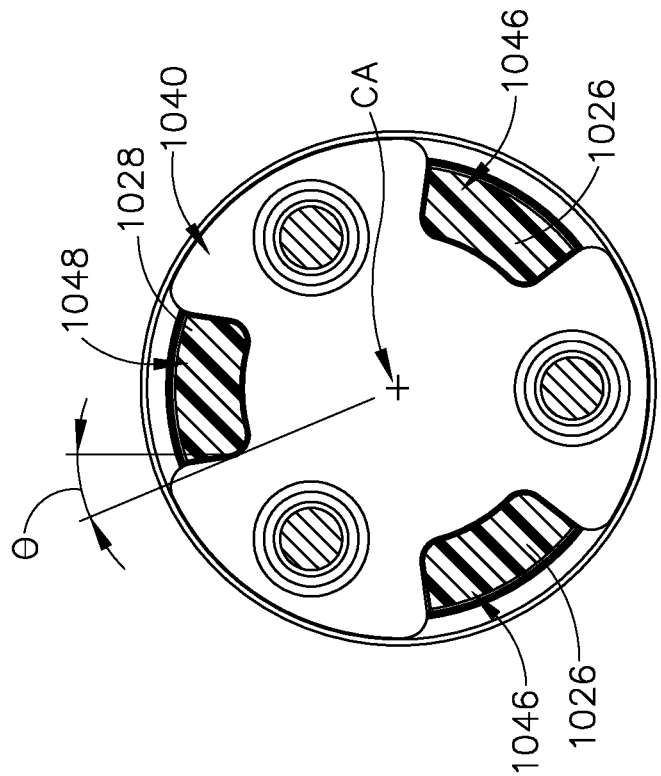
FIG. 19 depicts another cross-sectional view of the rotary drive assembly of FIG. 17, taken along line 19-19 of FIG. 17.
Figure 18:
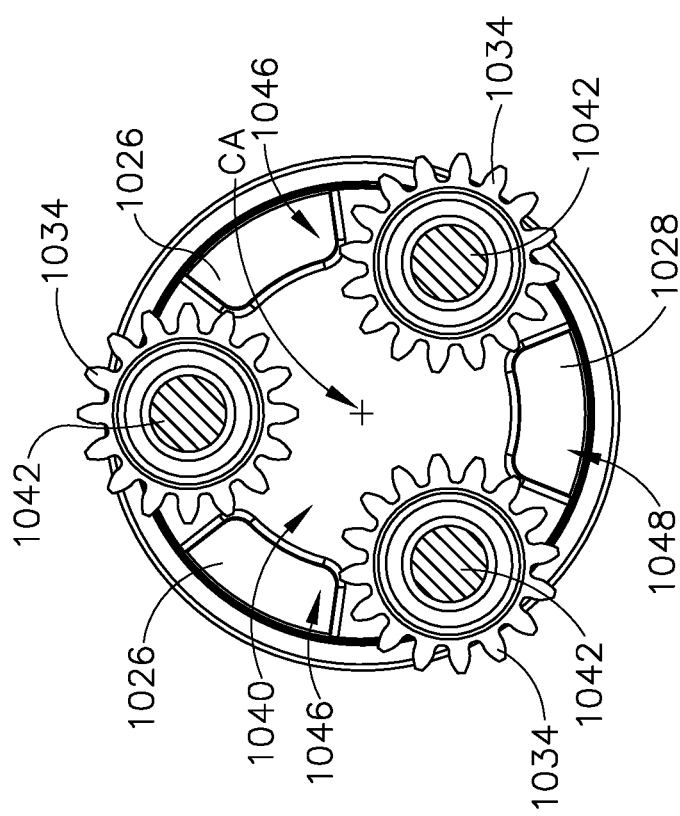
FIG. 18 depicts a cross-sectional view of the rotary drive assembly of FIG. 17, taken along line 18-18 of FIG. 17.

FIGS. 17-19 depict another exemplary rotary drive assembly (1000) that may be used to drive instrument (10). Rotary drive assembly (1000) may also be used to drive at least one rotary drive (210, 212), rotary drive spindle (356), rotary drive output (408, 808), or any other feature that is operable to receive a rotary drive. Rotary drive assembly (1000) of this example comprises a gearbox (1010) with an outer casing (1012) just like outer casing (912) described above. Rotary drive assembly (1000) also includes a driver (1020). Driver (1020) includes a pinion (1022) and a body (1024), with a set of downwardly extending tabs (1026, 1028) at the bottom end of body (1024). Driver (1020) also includes planetary gears (1034) secured to a rotary carrier (1040). As shown in FIGS. 18-19, carrier (1040) defines a set of notches (1046, 1048) that are configured to receive corresponding tabs (1026, 1028) of driver (1020). In this example, notches (1046) and tabs (1026) extend along a greater angular extent than notch (1048) and tab (1028). This configuration may provide a poke-yoke to ensure easy, consistent coupling of driver (1020) with carrier (1040), without requiring precise axial alignment. With tabs (1026, 1028) disposed in notches (1046, 1048), driver (1020) will rotate unitarily with carrier (1040) about the central axis (CA). With tabs (1026, 1028) and notches (1046, 1048) being positioned at the outer periphery of carrier (1040), the assembly may provide minimized torque induced loading on tabs (1026, 1028) and notches (1046, 1048). In addition, the combination of the motor (not shown) and gearbox (1010) may be easily tested without driver (1020) in place.

As also shown in FIG. 18, each planetary gear (1034) is rotatably mounted to a corresponding axle (1042) of carrier (1042). While not shown, planetary gears (1034) interiorly mesh with a sun gear, which is directly driven by a motor. Planetary gears (1034) exteriorly mesh with internal teeth (not shown) of casing (1012). Planetary gears (1034) thus rotate about the axis of each corresponding axle (1042) while also orbiting about the central axis (CA) when the motor is activated.

As shown in FIG. 18, notches (1046, 1048) are configured such that they do not overlap with the addendum circles of planetary gears (1034). Thus, in the event that tabs (1026, 1028) protrude downwardly to a point where tabs (1026, 1028) intersect a horizontal plane that passes through all planetary gears (1034), tabs (1026, 1028) will not engage or otherwise interfere with rotation of planetary gears (1034).

As shown in FIG. 19, the outer angular boundaries of tabs (1026, 1028) and notches (1046, 1048) are oriented along lines that are not coincident with radii extending from the central axis (CA). In particular, these outer angular boundaries of tabs (1026, 1028) and notches (1046, 1048) are oriented along lines that define an angle (θ) with the closest radius extending from the central axis (CA). This configuration may provide resistance to a radial separating force on tabs (1026, 1028) and notches (1046, 1048) that might otherwise occur as rotary drive assembly (1000) is driven. In other words, if the outer angular boundaries of tabs (1026, 1028) and notches (1046, 1048) were coincident with radii extending from the central axis (CA), tabs (1026, 1028) and notches (1046, 1048) might experience a radial separating force as rotary drive assembly (1000) is driven.

While three planetary gears (1034) are shown, any other suitable number of planetary gears (1034) may be used in each stage. In addition, while just one set of planetary gears (1034) and just one carrier (1040) are shown, any other suitable number of sets of planetary gears (1034) and carriers (1040) may be provided.

V. EXEMPLARY BATTERY WITH MULTIPLE STATES

A battery such as a battery found in battery pack (110) or internal power source (222, 412, 810) may be configured to transition between various states, depending on the circumstances at hand. Such states may include, but are not necessarily limited to, the following: a first state where the battery is not electrically connected to handle assembly (11, 200, 300, 400, 800); a second state where the battery is electrically connected to handle assembly (11, 200, 300, 400, 800) and is actively being used (e.g., to power motor (118, 224, 226, 302, 418, 814, 816, 902)); a third state where the battery is electrically connected to handle assembly (11, 200, 300, 400, 800) but is not actively being used; and a fourth state where the battery is removable for recycling or disposal.

By way of example only, a battery may be in the first state during shipping and while the battery is stored before use. In this state, the battery may be insulated from any current draw. In the present example, the operator must perform some action on the battery, beyond simply inserting the battery into handle assembly (11, 200, 300, 400, 800), to enable the battery to transition from the first state to the second state. Also in the present example, once the operator transitions the battery from the first state to the second state, the battery is unable to return to the first state. For instance, the battery may be configured to couple with handle assembly (11, 200, 300, 400, 800); but may also be configured to not be removable from handle assembly (11, 200, 300, 400, 800). Examples of features that may provide such functionality are disclosed in U.S. patent application Ser. No. 15/634, 475, entitled "Powered Surgical Instrument with Latching Feature Preventing Removal of Battery Pack," filed on Jun. 27, 2017, issued as U.S. Pat. No. 10,987,103 on Apr. 27, 2021, the disclosure of which is incorporated by reference herein. As another merely illustrative example, a removable electrical insulator may be positioned over electrical contacts of the battery to ensure that no closed circuit is formed between the contacts. The insulator must be removed before the battery can be coupled with handle assembly (11, 200, 300, 400, 800). Once the insulator is removed from the battery, the insulator cannot be recoupled with the battery.

After the battery is in the second state, a feature of battery pack (110), internal power source (222, 412, 810), and/or handle assembly (11, 200, 300, 400, 800) may be configured to transition handle assembly (11, 200, 300, 400, 800) to a low power drain "sleep" mode, with a means to power up after the sleep mode has been initiated. For instance, when a shaft assembly (16, 120, 130, 140, 230, 240, 250, 350, 500, 600, 700) is disconnected from handle assembly (11, 200, 300, 400, 800), handle assembly (11, 200, 300, 400, 800) may immediately de-energize high power contacts of electrical connector (108, 206, 340, 402, 802). As another merely illustrative example, when a shaft assembly (16, 120, 130, 140, 230, 240, 250, 350, 500, 600, 700) is disconnected from handle assembly (11, 200, 300, 400, 800), and another shaft assembly (16, 120, 130, 140, 230, 240, 250, 350, 500, 600, 700) is not coupled with handle assembly (11, 200, 300, 400, 800) after a certain duration, handle assembly (11, 200, 300, 400, 800) may transition to sleep mode.

The battery may reach the third state when shaft assembly (16, 120, 130, 140, 230, 240, 250, 350, 500, 600, 700) is coupled with handle assembly (11, 200, 300, 400, 800); or when shaft assembly (16, 120, 130, 140, 230, 240, 250, 350, 500, 600, 700) is not coupled with handle assembly (11, 200, 300, 400, 800). In the case where the battery is in the third state when shaft assembly (16, 120, 130, 140, 230, 240, 250, 350, 500, 600, 700) is not coupled with handle assembly (11, 200, 300, 400, 800), control circuit/module (117, 220, 410, 812) may prevent activation of the primary power up cycle even if the operator actuates a "power on" button or other user input feature. For instance, if a "power on" button or other user input feature is actuated when shaft assembly (16, 120, 130, 140, 230, 240, 250, 350, 500, 600, 700) is not coupled with handle assembly (11, 200, 300, 400, 800), a display (e.g., graphical user interface (116), flip-up screen (304), etc.) of handle assembly (11, 200, 300, 400, 800) may display the amount of life remaining in the battery, but the primary circuit will not be energized. Examples of configurations and methods for providing such operability are disclosed in U.S. patent application Ser. No. 15/634,418, entitled "Surgical Instrument with Integrated and Independently Powered Displays," filed Jun. 27, 2017, issued as U.S. Pat. No. 10,163,309 on Dec. 25, 2018, the disclosure of which is incorporated by reference herein. In some versions, a separate parallel flex circuit is coupled with features of handle assembly (11, 200, 300, 400, 800) that mechanically couple with shaft assembly (16, 120, 130, 140, 230, 240, 250, 350, 500, 600, 700) (e.g., attachment pin (42), etc.) and provides pins for the battery circuit to access to verify if a shaft assembly (16, 120, 130, 140, 230, 240, 250, 350, 500, 600, 700) is coupled with handle assembly (11, 200, 300, 400, 800) when the operator actuates a "power on" button or other user input feature.

VI. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus, comprising: (a) a body assembly, wherein the body assembly comprises: (i) a rotary drive output, (ii) a linear drive output, and (iii) a control module; (b) a shaft assembly, wherein the shaft assembly comprises: (i) a distal end, wherein the distal end includes a type of end effector configured to operate on tissue, and (ii) a proximal end, wherein the proximal end is configured to removably couple with the body assembly, wherein the proximal end comprises one or both of: (A) a rotary drive input configured to couple with the rotary drive output, or (B) a linear drive input configured to couple with the linear drive input, wherein the shaft assembly is configured to actuate the end effector in response to movement of one or both of the rotary drive input or the linear drive input; wherein the control module is configured to selectively actuate the rotary drive output or the linear drive output based on the type of end effector of the shaft assembly.

Example 2

The apparatus of Example 1, wherein the body assembly further comprises a first rotary motor, wherein the rotary motor is operable to drive one or both of the rotary drive output or the linear drive output.

Example 3

The apparatus of Example 2, wherein the body assembly further comprises a second rotary motor, wherein the first rotary motor is operable to drive the linear drive output, wherein the second rotary motor is operable to drive the rotary drive output.

Example 4

The apparatus of Example 3, wherein the body further comprises a linear actuator coupled with the rotary drive output, wherein the linear actuator is configured to drive the rotary drive output between a proximal position and a distal position.

Example 5

The apparatus of Example 4, wherein the body further defines an opening, wherein the rotary drive output is configured to be recessed relative to the opening when the rotary drive output is in the proximal position, wherein the rotary drive output is configured to protrude through the opening when the rotary drive output is in the distal position.

Example 6

The apparatus of any one or more of Examples 2 through 5, wherein the body assembly further comprises a transmission assembly, wherein the transmission assembly is operable to switch between a first state and a second state, wherein the transmission assembly is configured to couple the first rotary motor with the rotary drive output in the first state, wherein the transmission assembly is configured to couple the first rotary motor with the linear drive output in the second state.

Example 7

The apparatus of Example 6, wherein the transmission assembly is further operable to switch to a third state, wherein the transmission assembly is configured to couple the first rotary motor with both the rotary drive output and the linear drive output in the third state.

Example 8

The apparatus of any one or more of Examples 6 through 7, wherein the control module is in communication with the transmission assembly, wherein the control module is configured to switch the transmission assembly between the first state and the second state.

Example 9

The apparatus of any one or more of Examples 1 through 8, wherein the body further comprises a sensor in communication with the control module, wherein the sensor is configured to detect the type of end effector of the shaft assembly.

Example 10

The apparatus of any one or more of Examples 1 through 9, wherein the body further comprises an integral power source.

Example 11

The apparatus of Example 10, wherein the integral power source comprises a battery.

Example 12

The apparatus of any one or more of Examples 1 through 11, wherein the body further comprises at least two user input features, wherein at least one of the user input features is operable to trigger one or both of the rotary drive output or the linear drive output.

Example 13

The apparatus of Example 12, wherein the control module is configured to trigger a user notification indicating a particular user input feature of the at least two user input features, wherein the particular user input feature is associated with the type of end effector of the shaft assembly.

Example 14

The apparatus of any one or more of Examples 1 through 13, wherein the end effector is operable to apply staples to tissue.

Example 15

The apparatus of Example 14, wherein the end effector is further operable to cut tissue.

Example 16

A kit, the kit comprising: (a) a body assembly, wherein the body assembly comprises: (i) a rotary drive output, (ii) a linear drive output, and (iii) a control module; (b) a first shaft assembly, wherein the first shaft assembly comprises: (i) a distal end, wherein the distal end of the first shaft assembly includes a first type of end effector configured to operate on tissue, and (ii) a proximal end, wherein the proximal end of the first shaft assembly is configured to removably couple with the body assembly, wherein the proximal end of the first shaft assembly comprises a rotary drive input, wherein the first shaft assembly is configured to actuate the first type of end effector in response to movement of the rotary drive input; and (c) a second shaft assembly, wherein the second shaft assembly comprises: (i) a distal end, wherein the distal end of the second shaft assembly includes a second type of end effector configured to operate on tissue, and (ii) a proximal end, wherein the proximal end of the second shaft assembly is configured to removably couple with the body assembly, wherein the proximal end of the second shaft assembly comprises a linear drive input, wherein the second shaft assembly is configured to actuate the second type of end effector in response to movement of the linear drive input; wherein the control module is configured to selectively actuate the rotary drive output or the linear drive output based on whether the first or second shaft assembly is coupled with the body.

Example 17

The kit of Example 16, wherein the first type of end effector comprises a circular stapler end effector, wherein the second type of end effector comprises a linear stapler end effector.

Example 18

The kit of any one or more of Examples 16 through 17, wherein the first type of end effector comprises a linear stapler end effector, wherein the second type of end effector comprises a circular stapler end effector.

Example 19

A method comprising: (a) coupling a first shaft assembly with a body assembly, wherein the body assembly comprises a linear driver, wherein the first shaft assembly comprises a linear driver; (b) positioning an end effector of the first shaft assembly adjacent to tissue of a patient; (c) actuating the body assembly to cause movement of the linear driver of the body assembly, wherein movement of the linear driver of the body assembly causes movement of the linear driver of the first shaft assembly, wherein movement of the linear driver of the first shaft assembly causes actuation of the end effector of the first shaft assembly, wherein actuation of the end effector of the first shaft assembly affects the adjacent tissue of the patient; (d) removing the first shaft assembly from the body assembly; (e) coupling a second shaft assembly with the body assembly, wherein the body assembly further comprises a rotary driver, wherein the second shaft assembly comprises a rotary driver; (f) positioning an end effector of the second shaft assembly adjacent to tissue of a patient; and (g) actuating the body assembly to cause movement of the rotary driver of the body assembly, wherein movement of the rotary driver of the body assembly causes movement of the rotary driver of the second shaft assembly, wherein movement of the rotary driver of the second shaft assembly causes actuation of the end effector of the second shaft assembly, wherein actuation of the end effector of the second shaft assembly affects the adjacent tissue of the patient.

Example 20

The method of Example 19, wherein actuation of the end effector of the first shaft assembly or actuation of the end effector of the second shaft assembly drives staples into the adjacent tissue of the patient.

VII. MISCELLANEOUS

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

In addition to the foregoing, the teachings herein may be readily combined with the teachings of U.S. patent application Ser. No. 15/634,385, entitled "Apparatus and Method to Determine End of Life of Battery Powered Surgical Instrument," filed on Jun. 27, 2017, issued as U.S. Pat. No. 10,835,218 on Nov. 17, 2020, the disclosure of which is incorporated by reference herein. Various suitable ways in which the teachings herein may be combined with the teachings of U.S. patent application Ser. No. 15/634,385, issued as U.S. Pat. No. 10,835,218, will be apparent to those of ordinary skill in the art in view of the teachings herein.

In addition to the foregoing, the teachings herein may be readily combined with the teachings of U.S. patent application Ser. No. 15/634,418, entitled "Surgical Instrument with Integrated and Independently Powered Displays," filed on Jun. 27, 2017, issued as U.S. Pat. No. 10,163,309 on Dec. 25, 2018, the disclosure of which is incorporated by reference herein. Various suitable ways in which the teachings herein may be combined with the teachings of U.S. patent application Ser. No. 15/634,418, issued as U.S. Pat. No. 10,163,309, will be apparent to those of ordinary skill in the art in view of the teachings herein.

In addition to the foregoing, the teachings herein may be readily combined with the teachings of U.S. patent application Ser. No. 15/634,436, entitled "Battery Pack with Integrated Circuit Providing Sleep Mode to Battery Pack and Associated Surgical Instrument," filed on Jun. 27, 2017, issued as U.S. Pat. No. 10,639,018, on May 5, 2020, the disclosure of which is incorporated by reference herein. Various suitable ways in which the teachings herein may be combined with the teachings of U.S. patent application Ser. No. 15/634,436, issued as U.S. Pat. No. 10,639,018, will be apparent to those of ordinary skill in the art in view of the teachings herein.

In addition to the foregoing, the teachings herein may be readily combined with the teachings of U.S. patent application Ser. No. 15/634,452, entitled "Battery Powered Surgical Instrument with Dual Power Utilization Circuits for Dual Modes," filed on Jun. 27, 2017, issued as U.S. Pat. No. 10,511,065 on Dec. 17, 2019, the disclosure of which is incorporated by reference herein. Various suitable ways in which the teachings herein may be combined with the teachings of U.S. patent application Ser. No. 15/634,452, issued as U.S. Pat. No. 10,511,065, will be apparent to those of ordinary skill in the art in view of the teachings herein.

In addition to the foregoing, the teachings herein may be readily combined with the teachings of U.S. patent application Ser. No. 15/634,475, entitled "Powered Surgical Instrument with Latching Feature Preventing Removal of Battery Pack," filed on Jun. 27, 2017, issued as U.S. Pat. No. 10,987,103 on Apr. 27, 2021, the disclosure of which is incorporated by reference herein. Various suitable ways in which the teachings herein may be combined with the teachings of U.S. patent application Ser. No. 15/634,475, issued as U.S. Pat. No. 10,987,103, will be apparent to those of ordinary skill in the art in view of the teachings herein.

In addition to the foregoing, the teachings herein may be readily combined with the teachings of U.S. patent application Ser. No. 15/634,497, entitled "Modular Powered Electrical Connection for Surgical Instrument with Features to Prevent Electrical Discharge" filed on Jun. 27, 2017, issued as U.S. Pat. No. 10,667,812 on Jun. 2, 2020, the disclosure of which is incorporated by reference herein. Various suitable ways in which the teachings herein may be combined with the teachings of U.S. patent application Ser. No. 15/634,497, issued as U.S. Pat. No. 10,667,812, will be apparent to those of ordinary skill in the art in view of the teachings herein.

In addition to the foregoing, the teachings herein may be readily combined with the teachings of U.S. patent application Ser. No. 15/634,556, entitled "Powered Circular Stapler with Reciprocating Drive Member to Provide Independent Stapling and Cutting of Tissue," filed on Jun. 27, 2017, published as U.S. Pub. No. 2018/0368851 on Dec. 27, 2018 the disclosure of which is incorporated by reference herein. Various suitable ways in which the teachings herein may be combined with the teachings of U.S. patent application Ser. No. 15/634,556, published as U.S. Pub. No. 2018/0368851, will be apparent to those of ordinary skill in the art in view of the teachings herein.

In addition to the foregoing, the teachings herein may be readily combined with the teachings of U.S. patent application Ser. No. 15/634,620, entitled "Surgical Stapler with Independently Actuated Drivers to Provide Varying Staple Heights," filed on Jun. 27, 2017, issued as U.S. Pat. No. 10,828,029 on Nov. 10, 2020, the disclosure of which is incorporated by reference herein. Various suitable ways in which the teachings herein may be combined with the teachings of U.S. patent application Ser. No. 15/634,620, issued as U.S. Pat. No. 10,828,029, will be apparent to those of ordinary skill in the art in view of the teachings herein.

In addition to the foregoing, the teachings herein may be readily combined with the teachings of U.S. patent application Ser. No. 15/634,589, entitled "Surgical Instrument Handle Assembly with Feature to Clean Electrical Contacts at Modular Shaft Interface," filed on Jun. 27, 2017, issued as U.S. Pat. No. 10,090,616 on Oct. 2, 2018, the disclosure of which is incorporated by reference herein. Various suitable ways in which the teachings herein may be combined with the teachings of U.S. patent application Ser. No. 15/634,589, issued as U.S. Pat. No. 10,090,616, will be apparent to those of ordinary skill in the art in view of the teachings herein.

It should also be understood that any ranges of values referred to herein should be read to include the upper and lower boundaries of such ranges. For instance, a range expressed as ranging "between approximately 1.0 inches and approximately 1.5 inches" should be read to include approximately 1.0 inches and approximately 1.5 inches, in addition to including the values between those upper and lower boundaries.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. A kit, the kit comprising:
(a) a body assembly, wherein the body assembly comprises:
a rotary drive output,
(ii) a linear drive output, and
(iii) a control module configured to shift between operative engagement with the rotary drive output or the linear drive output;
(b) a first shaft assembly, wherein the first shaft assembly comprises:

(i) a distal end, wherein the distal end of the first shaft assembly includes a first type of end effector configured to operate on tissue, and (ii) a proximal end, wherein the proximal end of the first shaft assembly is configured to removably couple with the body assembly, wherein the proximal end of the first shaft assembly comprises a rotary drive input configured to be driven by the rotary drive output while coupled with the body assembly, wherein the first shaft assembly is configured to actuate the first type of end effector in response to movement of the rotary drive input; and (c) a second shaft assembly, wherein the second shaft assembly comprises:

(i) a distal end, wherein the distal end of the second shaft assembly includes a second type of end effector configured to operate on tissue, and (ii) a proximal end, wherein the proximal end of the second shaft assembly is configured to removably couple with the body assembly, wherein the proximal end of the second shaft assembly comprises a linear drive input configured to be driven by the linear drive output while coupled with the body assembly, wherein the second shaft assembly is configured to actuate the second type of end effector in response to movement of the linear drive input;

wherein the control module is configured to operatively engage and selectively actuate the rotary drive output or the linear drive output based on whether the first or second shaft assembly, respectively, is coupled with the body.

2. The kit of claim 1, wherein the first type of end effector comprises a circular stapler end effector, wherein the second type of end effector comprises a linear stapler end effector.

3. The kit of claim 1, wherein the first type of end effector comprises a linear stapler end effector, wherein the second type of end effector comprises a circular stapler end effector.

4. The kit of claim 1, wherein the body assembly comprises a first electrical connector, wherein the first electrical connector is configured to established communication with first shaft assembly when the body assembly is coupled to the first shaft assembly, wherein the first electrical connector is configured to establish communication with the second shaft assembly when the body assembly is coupled to the second shaft assembly.

5. The kit of claim 4, wherein the first shaft assembly comprises a second electrical connector configured to electrically connect with the first electrical connector when the body assembly is coupled to the first shaft assembly.

6. The kit of claim 5, wherein the second shaft assembly comprises a third electrical connector configured to electrically connect with the first electrical connector when the body assembly is coupled to the second shaft assembly.

7. The kit of claim 1, where the body assembly further comprises a clutch configured to drive the rotary drive output between a disengaged configuration and an engaged configuration, wherein the rotary drive output is configured to operatively couple with the rotary drive input of the first shaft assembly in the engaged configuration.

8. The kit of claim 7, wherein the control module is configured to activate the clutch in order to drive the rotary drive output between the disengaged configuration and the engaged configuration.

9. The kit of claim 8, wherein the control module is configured to activate the clutch in response to the first shaft assembly initially coupling with the body assembly.

10. The kit of claim 7, wherein a portion of the rotary drive output extends distally from a housing of the body assembly in the engaged configuration.

11. The kit of claim 1, wherein the control module is configured to activate the rotary drive output in response to detecting attachment of the first shaft assembly with the body assembly, and further configured to activate the linear drive output in response to detecting attachment of the second shaft assembly with the body assembly.

12. The kit of claim 1, wherein the rotary drive output comprises a rotary drive spindle.

13. The kit of claim 12, wherein the rotary drive output comprises a first motor configured to rotate the rotary drive spindle.

14. The kit of claim 13, wherein the rotary drive output comprises a clutch operatively coupled to both the first motor and the rotary drive spindle.

15. The kit of claim 14, wherein the rotary drive input of the first shaft assembly comprises a second rotary drive spindle configured to selectively engage the rotary drive spindle of the rotary drive output.

16. The kit of claim 1, wherein the first shaft further comprises a second linear drive input configured to selectively engage the linear drive output of the body assembly.

17. A kit, the kit comprising:

(a) a body assembly, wherein the body assembly comprises:

(i) a rotary drive output, (ii) a linear drive output, and (iii) a control module;

(b) a first shaft assembly, wherein the first shaft assembly comprises:

(i) a first end effector actuatable to staple tissue, (ii) a first proximal end configured to removably couple with the body assembly, wherein the first proximal end of the first shaft assembly comprises a rotary drive input configured to operatively couple with the rotary drive output of the body assembly in order to drive the first end effector; and (c) a second shaft assembly, wherein the second shaft assembly comprises:

(i) a second end effector actuatable to staple tissue, and (ii) a second proximal end configured to removably couple with the body assembly, wherein the second proximal end of the second shaft assembly comprises a linear drive input configured to operatively couple with the linear drive output of the body assembly in order to drive the second end effector; and wherein the control module is configured to selectively actuate the rotary drive output or the linear drive output based on whether the first or second shaft assembly is coupled with the body, wherein the control module is configured to activate the rotary drive output in response to detecting attachment of the first shaft assembly with the body assembly to thereby drive the rotary drive input of the first proximal end of the first shaft assembly, and wherein the control module is configured to activate the linear drive output in response to detecting attachment of the second shaft assembly with the body assembly to thereby drive the linear drive input of the second proximal end of the second shaft assembly.

18. The kit of claim 17, wherein the linear drive output comprises a cradle.

19. The kit of claim 18, wherein the rotary drive output is configured to actuate relative to the linear drive output in order to operatively engage the rotary drive input of the first shaft assembly.

20. A kit, the kit comprising:
(a) a body assembly, wherein the body assembly comprises:
(i) a first drive output,
(ii) a second drive output, and
(iii) a control module configured to activate the first drive output and the second drive output;
(b) a first shaft assembly, wherein the first shaft assembly comprises:
(i) a first end effector actuatable to staple tissue, and
(ii) a first proximal end configured to removably couple with the body assembly, wherein the first proximal end of the first shaft assembly comprises a first drive input configured to operatively couple with the first drive output of the body assembly in order to drive the first end effector; and
(c) a second shaft assembly, wherein the second shaft assembly comprises:
(i) a second end effector actuatable to staple tissue, and
(ii) a second proximal end configured to removably couple with the body assembly, wherein the second proximal end of the second shaft assembly comprises a second drive input configured to operatively couple with the second drive output of the body assembly in order to drive the second end effector; and
wherein the control module is configured to selectively shift between actuating the first drive output or the second drive output based on whether the first or second shaft assembly is coupled with the body,
wherein the control module is configured to activate the first drive output in response to detecting attachment of the first shaft assembly with the body assembly to thereby drive the first drive input of the first proximal end of the first shaft assembly, and
wherein the control module is configured to activate the second drive output in response to detecting attachment of the second shaft assembly with the body assembly to thereby drive the second drive input of the second proximal end of the second shaft assembly.

* * * * *